(12) United States Patent
Samuel et al.

(10) Patent No.: US 8,686,222 B2
(45) Date of Patent: Apr. 1, 2014

(54) USE OF DENDRIMER NANOTECHNOLOGY FOR DELIVERY OF BIOMOLECULES INTO PLANT CELLS

(75) Inventors: Jayakumar P. Samuel, Carmel, IN (US); Narasimha C. Samboju, Carmel, IN (US); Kerrm Y. Yau, Carmel, IN (US); Steven R. Webb, Westfield, IN (US); Frank Burroughs, Noblesville, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 410 days.

(21) Appl. No.: 12/901,312

(22) Filed: Oct. 8, 2010

(65) Prior Publication Data

US 2011/0093982 A1     Apr. 21, 2011

Related U.S. Application Data

(60) Provisional application No. 61/252,607, filed on Oct. 16, 2009.

(51) Int. Cl.
*C12N 5/10* (2006.01)
*B82Y 5/00* (2011.01)

(52) U.S. Cl.
USPC ........ 800/278; 800/293; 800/320.1; 800/285; 977/754; 977/705; 435/430.1

(58) Field of Classification Search
None
See application file for complete search history.

(56) References Cited

U.S. PATENT DOCUMENTS

| | | |
|---|---|---|
| 4,769,061 A | 9/1988 | Comai |
| 4,810,648 A | 3/1989 | Stalker |
| 4,940,835 A | 7/1990 | Shah et al. |
| 4,975,374 A | 12/1990 | Goodman et al. |
| 5,266,317 A | 11/1993 | Tomalski et al. |
| 5,494,813 A | 2/1996 | Hepher et al. |
| 5,990,089 A | 11/1999 | Szoka, Jr. et al. |
| 6,248,846 B1 | 6/2001 | Zharov et al. |
| 6,316,694 B1 | 11/2001 | Dormann et al. |
| 2003/0009783 A1 | 1/2003 | Daniell et al. |
| 2003/0059940 A1 | 3/2003 | de Jong et al. |
| 2003/0096280 A1 | 5/2003 | Weber et al. |
| 2005/0260758 A1 | 11/2005 | Rasochova et al. |

FOREIGN PATENT DOCUMENTS

| | | |
|---|---|---|
| EP | 0 242 246 | 10/1987 |
| EP | 0 333 033 | 9/1989 |
| EP | 1577384 A1 | 9/2005 |
| WO | WO 93/02197 | 2/1993 |
| WO | WO 93/19181 | 9/1993 |
| WO | WO 94/00992 | 1/1994 |
| WO | WO 95/16776 | 6/1995 |
| WO | WO 95/18855 | 7/1995 |
| WO | WO 96/30517 | 10/1996 |
| WO | WO 96/30530 | 10/1996 |
| WO | WO 2005012515 | 2/2005 |
| WO | WO 2005107437 | 11/2005 |
| WO | 2008148223 A1 | 12/2008 |

OTHER PUBLICATIONS

Pasupathy et al. (Biotechnol. J. 2008, 3, 1078-1082, published online: Jun. 9, 2008).*
Svab et al. (Proc. Natl. Acad. Sci. USA vol. 87, pp. 8526-8530, Nov. 1990).*
Juliano (Ann. N.Y. Acad. Sci. (2006) 1082: pp. 18-26).*
Chugh et al. (FEBS Journal 275 (Feb. 2008), pp. 2403-2414).*
Atanassova et al., "A 126 by fragment of a plant histone gene promoter confers preferential expression in meristems of transgenic Arabidopsis" Plant Journal 2 (3):291 300 (1992).
C. Rudolph, C. Plank, J. Lausier, U. Schillinger, R.H. Müller, and J. Rosenecker (2003), Oligomers of the Arginine Rich Motif of the HIV 1 TAT Protein are Capable of Transferring Plasmid DNA into Cells, J. Biol. Chem. 278:11411-11418.
International Search Report and Written Opinion for PCT/US2010/051655 dated Jul. 27, 2011.
Chen et al., Transfection and expression of plasmid DNA in plant cells by an arginine-rich intracellular delivery peptide without protoplast preparation, vol. 581, No. 9, Apr. 21, 2007, 1891-1897.
Anonymous, Superlect Transfection Reagent Handbook, Quiagen, 2002, pp. 1-32 <http://www.qiagen.com/resources/Download.aspx?id={997AFE26-7D11-4BF7-A018-0AACAA57265E}lang=en&ver=1>.
Extended European Search Report for corresponding EP Application No. EP10823848.6, mailed Jun. 5, 2013.

* cited by examiner

*Primary Examiner* — David T Fox
*Assistant Examiner* — Jared Shapiro
(74) *Attorney, Agent, or Firm* — Ronald S. Maciak; TraskBritt, P.C.

(57) ABSTRACT

Provided are methods for introducing a molecule of interest into a plant cell having a cell wall by using dendrimers, and optionally one or more Cell Penetrating Peptides (CPPs). Methods are provided for genetically or otherwise modifying plants and for treating or preventing disease in plant cells comprising a cell wall.

20 Claims, 4 Drawing Sheets

SEQUENCE LISTING

<160> NUMBER OF SEQ ID NOS: 8

<210> SEQ ID NO 1
<211> LENGTH: 8448
<212> TYPE: DNA
<213> ORGANISM: Artificial Sequence
<220> FEATURE:
<223> OTHER INFORMATION: Plasmid pDAB3831

<400> SEQUENCE: 1

| | | | | | |
|---|---|---|---|---|---|
| ggccgctaaa | cccagaaggt | aattatccaa | gatgtagcat | caagaatcca | atgtttacgg | 60 |
| gaaaaactat | ggaagtatta | tgtaagctca | gcaagaagca | gatcaatatg | cggcacatat | 120 |
| gcaacctatg | ttcaaaaatg | aagaatgtac | agatacaaga | tcctatactg | ccagaatacg | 180 |
| aagaagaata | cgtagaaatt | gaaaagaag | aaccaggcga | agaaaagaat | cttgaagacg | 240 |
| taagcactga | cgacaacaat | gaaaagaaga | agataaggtc | ggtgattgtg | aaagagacat | 300 |
| agaggacaca | tgtaaggtgg | aaaatgtaag | ggcggaaagt | aaccttatca | caaggaatc | 360 |
| ttatccccca | ctacttatcc | ttttatattt | ttccgtgtca | tttttgcccct | tgagttttcc | 420 |
| tatataagga | accaagttcg | gcatttgtga | aaacaagaaa | aaatttggtg | taagctattt | 480 |
| tctttgaagt | actgaggata | caacttcaga | gaaatttgta | agtttgtaga | tctccatggg | 540 |
| ctccagcggc | gccctgctgt | tccacggcaa | gatcccctac | gtggtggaga | tggagggcaa | 600 |
| tgtggatggc | cacaccttca | gcatccgcgg | caagggctac | ggcgatgcca | gcgtgggcaa | 660 |
| ggtggatgcc | cagttcatct | gcaccaccgg | cgatgtgccc | gtgccctgga | gcaccctggt | 720 |
| gaccaccctg | acctacgcg | cccagtgctt | cgccaagtac | ggccccgagc | tgaaggattt | 780 |
| ctacaagagc | tgcatgcccg | atggctacgt | gcaggagcgc | accatcacct | tcgagggcga | 840 |
| tggcaatttc | aagacccgcg | ccgaggtgac | cttcgagaat | ggcagcgtgt | acaatcgcgt | 900 |
| gaagctgaat | ggccagggct | tcaagaagga | tggccacgtg | ctgggcaaga | atctggagtt | 960 |
| caatttcacc | ccccactgcc | tgtacatctg | gggcgatcag | gccaatcacg | gcctgaagag | 1020 |
| cgccttcaag | atctgccacg | agatcaccgg | cagcaagggc | gatttcatcg | tggccgatca | 1080 |
| cacccagatg | aatacccca | tcggcggcgg | ccccgtgcac | gtgcccgagt | accaccacat | 1140 |
| gagctaccac | gtgaagctga | gcaaggatgt | gaccgatcac | cgcgataata | tgagcctgaa | 1200 |
| ggagaccgtg | cgcgccgtgg | attgccgcaa | gacctacctg | tgagagctcg | catgcggtca | 1260 |
| ccaaaccttg | gactcccatg | ttggcaaagg | caaccaaaca | aacaatgaat | gatccgctcc | 1320 |
| tgcatatggg | gcggtttgag | tatttcaact | gccatttggg | ctgaattgaa | gacatgctcc | 1380 |
| tgtcagaaat | tccgtgatct | tactcaatat | tcagtaatct | cggccaatat | cctaaatgtg | 1440 |
| cgtggctta | tctgtctttg | tattgtttca | tcaattcatg | taacgtttgc | ttttcatatg | 1500 |
| aattttcaaa | taaattatcg | cgatagtact | acgaatattt | cgtatcgctg | atcttctcaa | 1560 |
| tcacaatgat | gcgtagtgac | ccgacaaata | atttaagcgt | ccttaatacc | aatcctaaaa | 1620 |
| taattgaggc | aaataaaatt | ttttgtaat | ttttatgata | gcagatcgat | tctccagcaa | 1680 |
| gcctgcaaca | aaatattgtg | tatttctaaa | tagatttga | tattaaaatc | ccgagaaagc | 1740 |
| aaaattgcat | ttaacaaaac | agtaatttag | tacattaata | aaaattatgc | tcggccggcc | 1800 |
| gcggccgctt | aattaaattt | aaatgtttaa | accccgcctg | caggtcaacg | gatcaggata | 1860 |
| ttcttgttta | agatgttgaa | ctctatggag | gtttgtatga | actgatgatc | taggaccgga | 1920 |
| taagttccct | tcttcatagc | gaacttattc | aaagaatgtt | ttgtgtatca | ttcttgttac | 1980 |

```
attgttatta atgaaaaaat attattggtc attggactga acacgagtgt taaatatgga    2040
ccaggcccca aataagatcc attgatatat gaattaaata acaagaataa atcgagtcac    2100
caaaccactt gcctttttta acgagacttg ttcaccaact tgatacaaaa gtcattatcc    2160
tatgcaaatc aataatcata caaaaatatc aataacact  aaaaaattaa aagaaatgga    2220
taatttcaca atatgttata cgataaagaa gttacttttc caagaaattc actgattta    2280 taagcccact tgcattagat aaatggcaaa aaaaacaaa aaggaaaaga aataaagcac     2340
gaagaattct agaaaatacg aaatacgctt caatgcagtg ggacccacgg ttcaattatt    2400 gccaatttc agctccaccg tatatttaaa aaataaaacg ataatgctaa aaaaatataa     2460
atcgtaacga tcgttaaatc tcaacggctg gatcttatga cgaccgttag aaattgtggt    2520
tgtcgacgag tcagtaataa acggcgtcaa agtggttgca gccggcacac acgagtcgtg    2580
tttatcaact caaagcacaa atacttttcc tcaacctaaa aataaggcaa ttagccaaaa    2640
acaactttgc gtgtaaacaa cgctcaatac acgtgtcatt ttattattag ctattgcttc    2700
accgccttag cttcctcgtg acctagtcgt cctcgtcttt tcttcttctt cttctataaa    2760
acaatcccca aagcttcttc ttcacaattc agatttcaat ttctcaaaat cttaaaaact    2820
ttctctcaat tctctctacc gtgatcaagg taaatttctg tgttccttat tctctcaaaa    2880
tcttcgattt tgttttcgtt cgatcccaat ttcgtatatg ttctttggtt tagattctgt    2940
taatcttaga tcgaagacga ttttctgggt ttgatcgtta gatatcatct taattctcga    3000
ttagggtttc ataaatatca tccgatttgt tcaaataatt tgagttttgt cgaataatta    3060
ctcttcgatt tgtgatttct atctagatct ggtgttagtt tctagtttgt gcgatcgaat    3120
ttgtcgatta atctgagttt ttctgattaa caggtaagga tccaaccatg gcttctccgg    3180
agaggagacc agttgagatt aggccagcta cagcagctga tatggccgcg gtttgtgata    3240
tcgttaacca ttacattgag acgtctacag tgaactttag gacagagcca caaacaccac    3300
aagagtggat tgatgatcta gagaggttgc aagatagata cccttggttg gttgctgagg    3360
ttgagggtgt tgtggctggt attgcttacg ctgggccctg gaaggctagg aacgcttacg    3420
attggacagt tgagagtact gtttacgtgt cacataggca tcaaaggttg ggcctaggat    3480
ccacattgta cacacatttg cttaagtcta tggaggcgca aggttttaag tctgtggttg    3540
ctgttatagg ccttccaaac gatccatctg ttaggttgca tgaggctttg ggatacacag    3600 cccgggtac attgcgcgca gctggataca agcatggtgg atggcatgat gttggttttt     3660
ggcaaaggga ttttgagttg ccagctcctc caaggccagt taggccagtt acccagatct    3720
gaggtaccct gagcttgagc ttatgagctt atgagcttag agctcggatc cactagtaac    3780
ggccgccagt gtgctggaat tcgcccttga ctagataggc gcccagatcg gcggcaatag    3840
cttcttagcg ccatcccggg ttgatcctat ctgtgttgaa atagttgcgg tgggcaaggc    3900
tctctttcag aaagacaggc ggccaaagga acccaaggtg aggtgggcta tggctctcag    3960
ttccttgtgg aagcgcttgg tctaaggtgc agaggtgtta gcgggatgaa gcaaaagtgt    4020
ccgattgtaa caagatatgt tgatcctacg taaggatatt aaagtatgta ttcatcacta    4080
atataatcag tgtattccaa tatgtactac gatttccaat gtctttattg tcgccgtatg    4140
taatcggcgt cacaaaataa tccccggtga ctttcttta  atccaggatg aaataatatg    4200
ttattataat ttttgcgatt tggtccgtta taggaattga agtgtgcttg cggtcgccac    4260
cactcccatt tcataatttt acatgtattt gaaaaataaa aatttatggt attcaattta    4320
aacacgtata cttgtaaaga atgatatctt gaaagaaata tagtttaaat atttattgat    4380
```

```
aaaataacaa gtcaggtatt atagtccaag caaaaacata aatttattga tgcaagttta      4440
aattcagaaa tatttcaata actgattata tcagctggta cattgccgta gatgaaagac      4500
tgagtgcgat attatggtgt aatacatagc ggccgggttt ctagtcaccg gtgtagcttg      4560
gcgtaatcat ggtcatagct gtttcctgtg tgaaattgtt atccgctcac aattccacac      4620
aacatacgag ccggaagcat aaagtgtaaa gcctggggtg cctaatgagt gagctaactc      4680
acattaattg cgttgcgctc actgcccgct ttccagtcgg gaaacctgtc gtgccagctg      4740
cattaatgaa tcggccaacg cgcggggaga ggcggtttgc gtattgggcg ctcttccgct      4800 cgcacgctg cgcacgctgc gcacgcttcc tcgctcactg actcgctgcg ctcggtcgtt      4860
cggctgcggc gagcggtatc agctcactca aaggcggtaa tacggttatc cacagaatca      4920
ggggataacg caggaaagaa catgtgagca aaaggccagc aaaaggccag gaaccgtaaa      4980
aaggccgcgt tgctggcgtt tttccatagg ctccgccccc ctgacgagca tcacaaaaat      5040
cgacgctcaa gtcagaggtg gcgaaacccg acaggactat aaagatacca ggcgtttccc      5100
cctggaagct ccctcgtgcg ctctcctgtt ccgaccctgc cgcttaccgg atacctgtcc      5160
gcctttctcc cttcgggaag cgtggcgctt tctcatagct cacgctgtag gtatctcagt      5220
tcggtgtagg tcgttcgctc caagctgggc tgtgtgcacg aaccccccgt tcagcccgac      5280
cgctgcgcct tatccggtaa ctatcgtctt gagtccaacc cggtaagaca cgacttatcg      5340
ccactggcag cagccactgg taacaggatt agcagagcga ggtatgtagg cggtgctaca      5400
gagttcttga agtggtggcc taactacggc tacactagaa ggacagtatt tggtatctgc      5460
gctctgctga agccagttac cttcggaaaa agagttggta gctcttgatc cggcaaacaa      5520
accaccgctg gtagcggtgg tttttttgtt tgcaagcagc agattacgcg cagaaaaaaa      5580
ggatctcaag aagatccttt gatcttttct acggggtctg acgctcagtg gaacgaaaac      5640
tcacgttaag ggattttggt catgagatta tcaaaaagga tcttcaccta gatccttta      5700 aattaaaaat gaagttttaa atcaatctaa agtatatatg agtaaacttg gtctgacagt      5760
taccaatgct taatcagtga ggcacctatc tcagcgatct gtctatttcg ttcatccata      5820
gttgcctgac tccccgtcgt gtagataact acgatacggg agggcttacc atctggcccc      5880
agtgctgcaa tgataccgcg agacccacgc tcaccggctc cagatttatc agcaataaac      5940
cagccagccg gaagggccga gcgcagaagt ggtcctgcaa ctttatccgc ctccatccag      6000
tctattaatt gttgccggga agctagagta agtagttcgc cagttaatag tttgcgcaac      6060
gttgttgcca ttgctacagg catcgtggtg tcacgctcgt cgtttggtat ggcttcattc      6120
agctccggtt cccaacgatc aaggcgagtt acatgatccc ccatgttgtg caaaaaagcg      6180
gttagctcct tcggtcctcc gatcgttgtc agaagtaagt tggccgcagt gttatcactc      6240
atggttatgg cagcactgca taattctctt actgtcatgc catccgtaag atgcttttct      6300
gtgactggtg agtactcaac caagtcattc tgagaatagt gtatgcggcg accgagttgc      6360
tcttgcccgg cgtcaatacg ggataatacc gcgccacata gcagaacttt aaaagtgctc      6420
atcattggaa aacgttcttc ggggcgaaaa ctctcaagga tcttaccgct gttgagatcc      6480
agttcgatgt aacccactcg tgcacccaac tgatcttcag catctttta tttcaccagc      6540 gtttctgggg gagcaaaaac aggaaggcaa aatgccgcaa aaagggaat aagggcgaca      6600 cggaaatgtt gaatactcat actcttcctt tttcaatatt attgaagcat ttatcagggt      6660
tattgtctca tgagcggata catatttgaa tgtatttaga aaaataaaca aataggggtt      6720
ccgcgcacat ttccccgaaa agtgccacct gacgtctaag aaaccattat tatcatgaca      6780
```

```
ttaacctata aaaataggcg tatcacgagg cccttccgtc tcgcgcgttt cggtgatgac    6840
ggtgaaaacc tctgacacat gcagctcccg gagacggtca cagcttgtct gtaagcggat    6900
gccgggagca gacaagcccg tcagggcgcg tcagcgggtg ttggcgggtg tcggggctgg    6960
cttaactatg cggcatcaga gcagattgta ctgagagtgc accatatgcg gtgtgaaata    7020
ccgcacagat gcgtaaggag aaaataccgc atcaggcgcc attcgccatt caggctgcgc    7080
aactgttggg aagggcgatc ggtgcgggcc tcttcgctat tacgccagct ggcgaaaggg    7140
ggatgtgctg caaggcgatt aagttgggta acgccagggt tttcccagtc acgacgttgt    7200
aaaacgacgg ccagtgaatt acaccggtgt gatcatgggc cgcgattaaa aatctcaatt    7260
atatttggtc taatttagtt tggtattgag taaaacaaat tcgaaccaaa ccaaaatata    7320
aatatatagt ttttatatat atgcctttaa gacttttat agaattttct ttaaaaaata    7380
tctagaaata tttgcgactc ttctggcatg taatatttcg ttaaatatga agtgctccat    7440
ttttattaac tttaaataat tggttgtacg atcactttct tatcaagtgt tactaaaatg    7500
cgtcaatctc tttgttcttc catattcata tgtcaaaacc tatcaaaatt cttatatatc    7560
tttttcgaat ttgaagtgaa atttcgataa tttaaaatta aatagaacat atcattattt    7620
aggtatcata ttgattttta tacttaatta ctaaatttgg ttaactttga aagtgtacat    7680
caacgaaaaa ttagtcaaac gactaaaata aataaatatc atgtgttatt aagaaaattc    7740
tcctataaga atatttaat agatcatatg tttgtaaaaa aaattaattt ttactaacac    7800
atatatttac ttatcaaaaa tttgacaaag taagattaaa ataatattca tctaacaaaa    7860
aaaaaaccag aaaatgctga aaacccggca aaacgaacc aatccaaacc gatatagttg    7920
gtttggtttg attttgatat aaaccgaacc aactcggtcc atttgcaccc ctaatcataa    7980
tagctttaat atttcaagat attattaagt taacgttgtc aatatcctgg aaattttgca    8040
aaatgaatca agcctatatg gctgtaatat gaatttaaaa gcagctcgat gtggtggtaa    8100
tatgtaattt acttgattct aaaaaaatat cccaagtatt aataatttct gctaggaaga    8160
aggttagcta cgatttacag caaagccaga atacaatgaa ccataaagtg attgaagctc    8220
gaaatatacg aaggaacaaa tattttaaaa aaaatacgca atgacttgga acaaaagaaa    8280
gtgatatatt ttttgttctt aaacaagcat cccctctaaa gaatggcagt tttcctttgc    8340
atgtaactat tatgctccct tcgttacaaa aattttggac tactattggg aacttcttct    8400
gaaaatagtg gccaccgctt aattaaggcg cgccatgccc gggcaagc                 8448
```

<210> SEQ ID NO 2
<211> LENGTH: 8448
<212> TYPE: DNA
<213> ORGANISM: Artificial sequence
<220> FEATURE:
<223> OTHER INFORMATION: reverse complement of SEQ ID NO: 1

<400> SEQUENCE: 2

```
gcttgcccgg gcatggcgcg ccttaattaa gcggtggcca ctattttcag aagaagttcc      60
caatagtagt ccaaaatttt tgtaacgaag ggagcataat agttacatgc aaaggaaaac     120
tgccattctt tagaggggat gcttgtttaa gaacaaaaaa tatatcactt tcttttgttc     180
caagtcattg cgtatttttt taaaatatt tgttccttcg tatatttcga gcttcaatca     240
ctttatggtt cattgtattc tggctttgct gtaaatcgta gctaaccttc ttcctagcag     300
aaattattaa tacttgggat attttttag aatcaagtaa attacatatt accaccacat     360
cgagctgctt ttaaattcat attacagcca tataggcttg attcattttg caaaattcc      420
```

```
aggatattga caacgttaac ttaataatat cttgaaatat taaagctatt atgattaggg      480
gtgcaaatgg accgagttgg ttcggtttat atcaaaatca aaccaaacca actatatcgg      540
tttggattgg ttcggttttg ccgggttttc agcattttct ggtttttttt tgttagatg       600 aatattattt taatcttact ttgtcaaatt tttgataagt aaatatatgt gttagtaaaa      660
attaattttt tttacaaaca tatgatctat taaaatattc ttataggaga atttctttaa      720
taacacatga tatttattta ttttagtcgt ttgactaatt tttcgttgat gtacactttc      780
aaagttaacc aaatttagta attaagtata aaaatcaata tgatacctaa ataatgatat      840
gttctattta atttttaaatt atcgaaattt cacttcaaat tcgaaaaaga tatataagaa     900
ttttgatagg ttttgacata tgaatatgga agaacaaaga gattgacgca ttttagtaac     960
acttgataag aaagtgatcg tacaaccaat tatttaaagt taataaaaat ggagcacttc     1020
atatttaacg aaatattaca tgccagaaga gtcgcaaata tttctagata ttttttaaag    1080
aaaattctat aaaaagtctt aaaggcatat atataaaaac tatatattta tattttggtt    1140
tggttcgaat ttgttttact caataccaaa ctaaattaga ccaaatataa ttgagatttt    1200
taatcgcggc ccatgatcac accggtgtaa ttcactggcc gtcgttttac aacgtcgtga    1260
ctgggaaaac cctggcgtta cccaacttaa tcgccttgca gcacatcccc ctttcgccag    1320
ctggcgtaat agcgaagagg cccgcaccga tcgcccttcc caacagttgc gcagcctgaa    1380
tggcgaatgg cgcctgatgc ggtattttct ccttacgcat ctgtgcggta tttcacaccg    1440
catatggtgc actctcagta caatctgctc tgatgccgca tagttaagcc agccccgaca    1500
cccgccaaca cccgctgacg cgccctgacg ggcttgtctg ctcccggcat ccgcttacag    1560
acaagctgtg accgtctccg ggagctgcat gtgtcagagg ttttcaccgt catcaccgaa    1620
acgcgcgaga cgaaagggcc tcgtgatacg cctatttta taggttaatg tcatgataat    1680
aatggtttct tagacgtcag gtggcacttt tcggggaaat gtgcgcggaa ccccctatttg   1740 tttattttc taaatacatt caaatatgta tccgctcatg agacaataac cctgataaat     1800
gcttcaataa tattgaaaaa ggaagagtat gagtattcaa catttccgtg tcgcccttat    1860
tccctttttt gcggcatttt gccttcctgt ttttgctcac ccagaaacgc tggtgaaagt    1920
aaaagatgct gaagatcagt tgggtgcacg agtgggttac atcgaactgg atctcaacag    1980
cggtaagatc cttgagagtt ttcgccccga gaacgttttt ccaatgatga gcacttttaa    2040
agttctgcta tgtggcgcgg tattatcccg tattgacgcc gggcaagagc aactcggtcg    2100
ccgcatacac tattctcaga atgacttggt tgagtactca ccagtcacag aaaagcatct    2160
tacggatggc atgacagtaa gagaattatg cagtgctgcc ataaccatga gtgataacac    2220
tgcggccaac ttacttctga caacgatcgg aggaccgaag gagctaaccg cttttttgca    2280
caacatgggg gatcatgtaa ctcgccttga tcgttgggaa ccggagctga atgaagccat    2340
accaaacgac gagcgtgaca ccacgatgcc tgtagcaatg gcaacaacgt tgcgcaaact    2400
attaactggc gaactactta ctctagcttc ccggcaacaa ttaatagact ggatggaggc    2460
ggataaagtt gcaggaccac ttctgcgctc ggcccttccg gctggctggt ttattgctga    2520
taaatctgga gccggtgagc gtgggtctcg cggtatcatt gcagcactgg ggccagatgg    2580
taagccctcc cgtatcgtag ttatctacac gacggggagt caggcaacta tggatgaacg    2640
aaatagacag atcgctgaga taggtgcctc actgattaag cattggtaac tgtcagacca    2700
agtttactca tatatacttt agattgattt aaaacttcat ttttaattta aaaggatcta    2760
ggtgaagatc cttttgata atctcatgac caaaatccct taacgtgagt tttcgttcca    2820
```

```
ctgagcgtca gaccccgtag aaaagatcaa aggatcttct tgagatcctt ttttctgcg    2880
cgtaatctgc tgcttgcaaa caaaaaaacc accgctacca gcggtggttt gtttgccgga   2940
tcaagagcta ccaactcttt ttccgaaggt aactggcttc agcagagcgc agataccaaa   3000
tactgtcctt ctagtgtagc cgtagttagg ccaccacttc aagaactctg tagcaccgcc   3060
tacatacctc gctctgctaa tcctgttacc agtggctgct gccagtggcg ataagtcgtg   3120
tcttaccggg ttggactcaa gacgatagtt accggataag gcgcagcggt cgggctgaac   3180
ggggggttcg tgcacacagc ccagcttgga gcgaacgacc tacaccgaac tgagatacct   3240
acagcgtgag ctatgagaaa gcgccacgct tcccgaaggg agaaaggcgg acaggtatcc   3300
ggtaagcggc agggtcggaa caggagagcg cacgagggag cttccagggg gaaacgcctg   3360
gtatctttat agtcctgtcg ggtttcgcca cctctgactt gagcgtcgat ttttgtgatg   3420
ctcgtcaggg gggcggagcc tatggaaaaa cgccagcaac gcggccttttt tacggttcct   3480
ggccttttgc tggccttttg ctcacatgtt ctttcctgcg ttatccctg attctgtgga    3540
taaccgtatt accgcctttg agtgagctga taccgctcgc cgcagccgaa cgaccgagcg   3600
cagcgagtca gtgagcgagg aagcgtgcgc agcgtgcgca gcgtgcgcag cggaagagcg   3660
cccaatacgc aaaccgcctc tccccgcgcg ttggccgatt cattaatgca gctggcacga   3720
caggtttccc gactggaaag cgggcagtga gcgcaacgca attaatgtga gttagctcac   3780
tcattaggca ccccaggctt tacactttat gcttccggct cgtatgttgt gtggaattgt   3840
gagcggataa caatttcaca caggaaacag ctatgaccat gattacgcca agctacaccg   3900
gtgactagaa acccggccgc tatgtattac accataatat cgcactcagt ctttcatcta   3960
cggcaatgta ccagctgata taatcagtta ttgaaatatt tctgaattta aacttgcatc   4020
aataaattta tgttttttgct tggactataa tacctgactt gttatttttat caataaatat   4080
ttaaactata tttctttcaa gatatcattc tttacaagta tacgtgttta aattgaatac   4140
cataaatttt tattttttcaa atacatgtaa aattatgaaa tgggagtggt ggcgaccgca   4200
agcacacttc aattcctata acggaccaaa tcgcaaaaat tataataaca tattatttca   4260
tcctggatta aagaaaagtc accggggatt attttgtgac gccgattaca tacggcgaca   4320
ataaagacat tggaaatcgt agtacatatt ggaatacact gattatatta gtgatgaata   4380
catacttttaa tatccttacg taggatcaac atatcttgtt acaatcggac acttttgctt   4440
catcccgcta acacctctgc accttagacc aagcgcttcc acaaggaact gagagccata   4500
gcccacctca ccttgggttc ctttggccgc ctgtctttct gaaagagagc cttgcccacc   4560
gcaactattt caacacagat aggatcaacc cgggatggcg ctaagaagct attgccgccg   4620
atctgggcgc ctatcagtc aagggcgaat tccagcacac tggcggccgt tactagtgga    4680
tccgagctct aagctcataa gctcataagc tcaagctcag ggtacctcag atctgggtaa   4740
ctggcctaac tggccttgga ggagctggca actcaaaatc cctttgccaa aaaccaacat   4800
catgccatcc accatgcttg tatccagctg cgcgcaatgt accccgggct gtgtatccca   4860
aagcctcatg caacctaaca gatggatcgt ttggaaggcc tataacagca accacagact   4920
taaaaccttg cgcctccata gacttaagca aatgtgtgta caatgtggat cctaggccca   4980
acctttgatg cctatgtgac acgtaaacag tactctcaac tgtccaatcg taagcgttcc   5040
tagccttcca gggcccagcg taagcaatac cagccacaac accctcaacc tcagcaacca   5100
accaagggta tctatcttgc aacctctcta gatcatcaat ccactcttgt ggtgtttgtg   5160
gctctgtcct aaagttcact gtagacgtct caatgtaatg gttaacgata tcacaaaccg   5220
```

-continued

```
cggccatatc agctgctgta gctggcctaa tctcaactgg tctcctctcc ggagaagcca    5280
tggttggatc cttacctgtt aatcagaaaa actcagatta atcgacaaat tcgatcgcac    5340
aaactagaaa ctaacaccag atctagatag aaatcacaaa tcgaagagta attattcgac    5400
aaaactcaaa ttatttgaac aaatcggatg atatttatga aaccctaatc gagaattaag    5460
atgatatcta acgatcaaac ccagaaaatc gtcttcgatc taagattaac agaatctaaa    5520
ccaaagaaca tatacgaaat tgggatcgaa cgaaaacaaa atcgaagatt ttgagagaat    5580
aaggaacaca gaaatttacc ttgatcacgg tagagagaat tgagagaaag ttttttaagat   5640 tttgagaaat tgaaatctga attgtgaaga agaagctttg ggtattgttt tatagaagaa    5700
gaagaagaaa agacgaggac gactaggtca cgagaaagct aaggcggtga agcaatagct    5760
aataataaaa tgcacgtgt attgagcgtt gtttacacgc aaagttgttt ttggctaatt     5820
gccttatttt taggttgagg aaaagtattt gtgctttgag ttgataaaca cgactcgtgt    5880
gtgccggctg caaccacttt gacgccgttt attactgact cgtcgacaac cacaatttct    5940
aacggtcgtc ataagatcca gccgttgaga tttaacgatc gttacgattt atattttttt    6000
agcattatcg ttttatttt taaatatacg gtggagctga aaattggcaa taattgaacc    6060
gtgggtccca ctgcattgaa gcgtatttcg tattttctag aattcttcgt gctttatttc    6120 ttttccttt tgttttttt tgccatttat ctaatgcaag tgggcttata aaatcagtga    6180
atttcttgga aaagtaactt ctttatcgta taacatattg tgaaattatc catttctttt    6240 aatttttag tgttattgga tattttgta tgattattga tttgcatagg ataatgactt    6300
ttgtatcaag ttggtgaaca agtctcgtta aaaaaggcaa gtggtttggt gactcgattt    6360
attcttgtta tttaattcat atatcaatgg atcttatttg gggcctggtc catatttaac    6420
actcgtgttc agtccaatga ccaataatat tttttcatta ataacaatgt aacaagaatg    6480
atacacaaaa cattctttga ataagttcgc tatgaagaag ggaacttatc cggtcctaga    6540
tcatcagttc atacaaacct ccatagagtt caacatctta aacaagaata tcctgatccg    6600
ttgacctgca ggcggggttt aaacatttaa atttaattaa gcggccgcgg ccggccgagc    6660 ataatttta ttaatgtact aaaattactgt tttgttaaat gcaattttgc tttctcggga    6720
ttttaatatc aaaatctatt tagaaataca caatattttg ttgcaggctt gctggagaat    6780
cgatctgcta tcataaaaat tacaaaaaaa ttttatttgc ctcaattatt ttaggattgg    6840
tattaaggac gcttaaatta tttgtcgggt cactacgcat cattgtgatt gagaagatca    6900
gcgatacgaa atattcgtag tactatcgcg ataatttatt tgaaaattca tatgaaaagc    6960
aaacgttaca tgaattgatg aaacaataca aagacagata aagccacgca catttaggat    7020
attggccgag attactgaat attgagtaag atcacgaat ttctgacagg agcatgtctt    7080
caattcagcc caaatggcag ttgaaatact caaaccgccc catatgcagg agcggatcat    7140
tcattgtttg tttggttgcc tttgccaaca tgggagtcca aggtttggtg accgcatgcg    7200
agctctcaca ggtaggtctt gcggcaatcc acggcgcgca cggtctcctt caggctcata    7260
ttatcgcggt gatcggtcac atccttgctc agcttcacgt ggtagctcat gtggtggtac    7320
tcgggcacgt gcacggggcc gccgccgatg ggggtattca tctgggtgtg atcggccacg    7380
atgaaatcgc ccttgctgcc ggtgatctcg tggcagatct tgaaggcgct cttcaggccg    7440
tgattggcct gatcgcccca gatgtacagg cagtgggggg tgaaattgaa ctccagattc    7500
ttgcccagca cgtggcccatc cttcttgaag ccctggccat tcagcttcac gcgattgtac    7560
acgctgccat tctcgaaggt cacctcggcg cgggtcttga aattgccatc gccctcgaag    7620
```

-continued

```
gtgatggtgc gctcctgcac gtagccatcg ggcatgcagc tcttgtagaa atccttcagc    7680
tcggggccgt acttggcgaa gcactgggcg ccgtaggtca gggtggtcac cagggtgctc    7740
cagggcacgg gcacatcgcc ggtggtgcag atgaactggg catccacctt gcccacgctg    7800
gcatcgccgt agcccttgcc gcggatgctg aaggtgtggc catccacatt gccctccatc    7860
tccaccacgt agggatcttg ccgtggaac agcagggcgc cgctggagcc catggagatc    7920
tacaaactta caatttctc tgaagttgta cctcagtac ttcaaagaaa atagcttaca     7980
ccaaattttt tcttgttttc acaaatgccg aacttggttc cttatatagg aaaactcaag    8040
ggcaaaaatg acacggaaaa atataaaagg ataagtagtg ggggataaga ttcctttgtg    8100
ataaggttac tttccgccct tacattttcc accttacatg tgtcctctat gtctctttca    8160
caatcaccga ccttatcttc tcttttcat tgttgtcgtc agtgcttacg tcttcaagat     8220
tcttttcttc gcctggttct tcttttcaa tttctacgta ttcttcttcg tattctggca    8280
gtataggatc ttgtatctgt acattcttca tttttgaaca taggttgcat atgtgccgca    8340
tattgatctg cttcttgctg agcttacata atacttccat agttttccc gtaaacattg     8400 gattcttgat gctacatctt ggataattac cttctgggtt tagcggcc               8448
```

<210> SEQ ID NO 3
<211> LENGTH: 20
<212> TYPE: DNA
<213> ORGANISM: Artificial Sequence
<220> FEATURE:
<223> OTHER INFORMATION: PAT selectable marker and PhiYFP expression
      cassett Forward primer

<400> SEQUENCE: 3
tgaaagtgta catcaacgaa                                              20

<210> SEQ ID NO 4
<211> LENGTH: 18
<212> TYPE: DNA
<213> ORGANISM: Artificial Sequence
<220> FEATURE:
<223> OTHER INFORMATION: PAT selectable marker and PhiYFP expression
      cassett Reverse primer

<400> SEQUENCE: 4
ccgcaactat ttcaacac                                                18

<210> SEQ ID NO 5
<211> LENGTH: 24
<212> TYPE: DNA
<213> ORGANISM: Artificial sequence
<220> FEATURE:
<223> OTHER INFORMATION: Forward primer for YFP

<400> SEQUENCE: 5
tgttccacgg caagatcccc tacg                                         24

<210> SEQ ID NO 6
<211> LENGTH: 24
<212> TYPE: DNA
<213> ORGANISM: Artificial sequence
<220> FEATURE:
<223> OTHER INFORMATION: Reverse primer for YFP

<400> SEQUENCE: 6
tattcatctg ggtgtgatcg gcca                                         24

<210> SEQ ID NO 7

```
<211> LENGTH: 24
<212> TYPE: DNA
<213> ORGANISM: Artificial sequence
<220> FEATURE:
<223> OTHER INFORMATION: Forward primer for PAT

<400> SEQUENCE: 7
ggagaggaga ccagttgaga ttag                                        24

<210> SEQ ID NO 8
<211> LENGTH: 24
<212> TYPE: DNA
<213> ORGANISM: Artificial sequence
<220> FEATURE:
<223> OTHER INFORMATION: Reverse primer for PAT

<400> SEQUENCE: 8
agatctgggt aactggccta actg                                        24
```

USE OF DENDRIMER NANOTECHNOLOGY FOR DELIVERY OF BIOMOLECULES INTO PLANT CELLS

CROSS-REFERENCE TO RELATED APPLICATION

This application claims the benefit of U.S. Provisional Patent Application Ser. No. 61/252,607, filed Oct. 16, 2009, the disclosure of which is hereby incorporated herein in its entirety by this reference.

BACKGROUND OF THE INVENTION

Nanoparticles have unique properties that have been exploited for use in the delivery of DNA to cells. Metal nanoparticles, such as gold (Au) nanoparticles have been used for DNA delivery because of their low cytotoxicity and ease of functionalization with various ligands of biological significance. In addition to metal nanoparticles, semiconductor nanoparticles (e.g., quantum dots) ("QD") within the size range of 3 nm to 5 nm have also been used as carriers to deliver molecules into cells. DNA and proteins can be linked to the ligand attached to the QD surface (see, e.g., F. Patolsky et al., *J. Am. Chem. Soc.* 125, 13918 (2003)).

Nanoparticles have been used to deliver plasmid DNA to a variety of animal cells. It has been found that when DNA coated Nanoparticles are incubated with cells not having a cell wall, the cells take up the Nanoparticles and begin expressing any genes encoded on the DNA. However, the contemporary plant gene delivery is challenging due to the presence of plant cell walls, which leads to the common reliance on invasive delivery means for genetic transformation of plants. Where nanoparticle-mediated delivery to cells normally having a cell wall is desired, the cell's wall is stripped before the addition of the particles to protoplasts of plant (see F. Tomey et al., *Nature Nanotechnol.* 2, (2007)). In plant cells, the cell wall stands as a barrier for the delivery of exogenously applied molecules. Many invasive methods, like gene gun (biolistics), microinjection, electroporation, and *Agrobacterium*, have been employed to achieve gene and small molecule delivery into these walled plant cells, but delivery of proteins has only been achieved by microinjection. Delivery of small molecules and proteins in the presence of a plant cell wall remains unexplored and would be advantageous in order to develop enabling technologies to be deployed in intact plant cell/tissue or organ for in vitro and in vivo manipulations.

Cell penetrating peptides (CPPs) are a novel and fast growing class of short peptides that are known to play an important role in translocation of a wide range of cargo complexes including proteins and DNA across the bio-membranes in mammalian and human cell lines. J. Schwartz and S. Zhang (2000), Peptide-Mediated Cellular Delivery, *Curr. Opin. Mol. Ther.* 2:162-167; Ü. Langel (2002), Preface in: Cell Penetrating Peptides; Processes and Applications, U. Langel, Editor, CRC Press, Boca Raton; E. Vives and B. Lebleu (2002), The Tat-Derived Cell-Penetrating Peptide in: Cell-Penetrating Peptides; Processes and Applications, Ü. Langel, Editor, CRC Press, Boca Raton: pp. 3-22. While CPPs have been shown to facilitate cargo delivery in mammalian cells, the use of CPP in plant cells for transfection studies has been limited by a number of factors. A major obstacle to adapting this technology to plants is that, unlike animal cells, plant cells present a dual barrier system (cell wall and plasma membrane) for the internalization of CPPs and their cargos. Therefore, CPPs must overcome these two barriers for efficient translocation. CPPs have been used in plant cells but typically rely on use of permeabilization agents and techniques with the use of CPPs to effectuate delivery of cargo delivery to the plant cells. The HIV-1 TAT protein transduction domain (PTD) is one of the most well studied translocating peptides. Recent reports have shown the potential of TAT-PTD and its oligomers for plasmid delivery by forming a complex with the negatively charged DNA in mammalian cells. I. Ignatovich, E. Dizhe, A. Pavlotskaya, B. Akifiev, S. Burov, S. Orlov, and A. Perevozchikov (2003), Complexes of Plasmid DNA with Basic Domain 47-57 of the HIV-1 Tat Protein are Transferred to Mammalian Cells by Endocytosis-mediated Pathways, *J. Biol. Chem.* 278:42625-42636; C. Rudolph, C. Plank, J. Lausier, U. Schillinger, R. H. Müller, and J. Rosenecker (2003), Oligomers of the Arginine-Rich Motif of the HIV-1 TAT Protein are Capable of Transferring Plasmid DNA into Cells, *J. Biol. Chem.* 278:11411-11418; Z. Siprashvili, F. Scholl, S. Oliver, A. Adams, C. Contag, P. Wender, and P. Khavari (2003), Gene Transfer via Reversible Plasmid Condensation with Cysteine-Flanked, Internally Spaced Arginine-Rich Peptides, *Hum. Gene. Ther.* 14 (13):1225-33; I. Hellgren, J. Gorman, and C. Sylvén (2004), Factors Controlling the Efficiency of Tat-mediated Plasmid DNA Transfer, *J. Drug Target.* 12 (1):39-47.

Dendrimers are "cascade molecules" with unique core-shell macromolecular architecture. Dendrimers were first created in the laboratory in 1979 by Donald Tomalia (D. A. Tomalia et al., Preprints of the 1$^{St}$ SPSJ Int'l Polymer conference, Society of Polymer Science, Japan, Kyoto, 1984, p. 65; see also U.S. Pat. No. 6,316,694). Dendrimers have been used to deliver DNA and other biomolecules into animal cells. However, the presence of plant cell walls has presented challenges to gene delivery in plants. Additionally, the stable genomic integration of transgenes using dendrimer-based delivery has not been reported or demonstrated in plants. Thus, there still remains a need for a method of stable incorporation of genes and other molecules of interest in plants through use of dendrimer-based delivery.

BRIEF SUMMARY OF THE INVENTION

The following embodiments are described in conjunction with systems, tools and methods that are meant to be exemplary and illustrative, and not limiting in scope.

The present invention relates to methods using dendrimers, and optionally one or more CPPs, to non-invasively deliver molecular substances into cells having a cell wall for stable incorporation of the molecular substances therein.

One embodiment of the invention includes a method of introducing a molecule of interest into a plant cell having a cell wall to effect stable transformation of a plant and seeds. The method includes providing the plant cell having a cell wall and interacting a dendrimer, and optionally one or more CPPs, with a molecule of interest to form an activated dendrimer structure. The cell and the activated dendrimer structure are placed in contact with each other, under conditions permitting the uptake of the same into the cell having the cell wall.

Another embodiment of the invention includes a method of stably expressing a gene. The method includes providing a plant cell having a cell wall and interacting a dendrimer, and optionally one or more CPPs, with a gene to form an activated dendrimer structure. The plant cell having a cell wall and the activated dendrimer structure are placed in contact with each other, and the dendrimer and the gene are placed under conditions permitting the uptake of the same into the plant cell having the cell wall. The gene in the progeny of a plant having the plant cell is then expressed.

Yet another embodiment of the invention includes a method for transferring a molecular substance into a plant cell. The method includes interacting a dendrimer, and optionally one or more CPPs, with a plasmid DNA to form an activated dendrimer structure. The activated dendrimer structure is placed in contact with an intact wall-bearing plant cell under conditions permitting the uptake of the dendrimer and a gene from the plasmid DNA into the plant cell.

In addition to the exemplary aspects and embodiments described above, further aspects and embodiments will become apparent in view of the following descriptions.

DETAILED DESCRIPTION OF THE INVENTION

Figure 1:
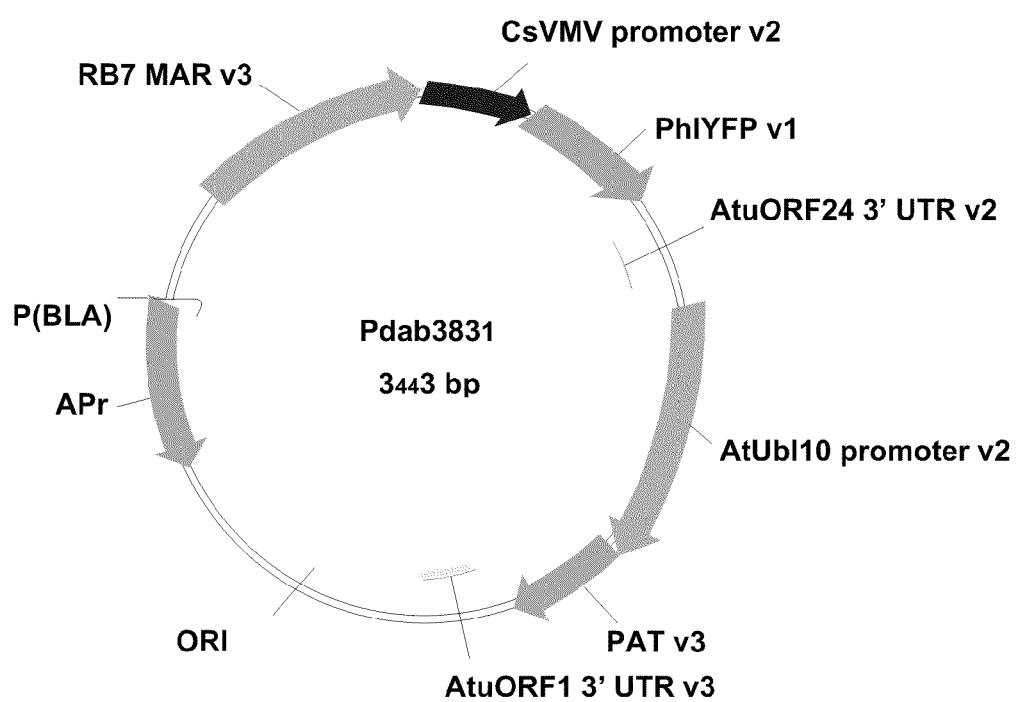
FIG. 1 shows Plasmid pDAB3831.

In the description and tables which follow, a number of terms are used. In order to provide a clear and consistent understanding of the specification and claims, including the scope to be given such terms, the following definitions are provided:

Backcrossing. Backcrossing may be a process in which a breeder repeatedly crosses hybrid progeny back to one of the parents, for example, a first generation hybrid $F_1$ with one of the parental genotypes of the $F_1$ hybrid.

Embryo. The embryo may be the small plant contained within a mature seed.

Dendrimer. Dendrimers are three-dimensional, hyperbranched, monodisperse nanometric macromolecules obtained by a reiterative sequence of reactions. Dendrimers are routinely synthesized as tunable "nanostructures" that may be designed and regulated as a function of their size, shape, surface chemistry and interior void space. Dendrimers can be obtained with structural control approaching that of traditional biomacromolecules, such as DNNPNA or proteins and are distinguished by their precise nanoscale scaffolding and nanocontainer properties. Dendrimers are microscopic particles with at least one nanoscale dimension, usually less than 100 nm. Dendrimers suitable for use in the present invention may have a size of 1 nm-0.4 µM.

Resistant to Glyphosate. Resistance to a dosage of glyphosate refers to the ability of a plant to survive (i.e., the plant may be not killed) by that dosage of glyphosate. In some cases, tolerant plants may temporarily yellow or otherwise exhibit some glyphosate-induced injury (e.g., excessive tillering and/or growth inhibition), but recover.

Stabilized. Stabilized refers to characteristics of a plant that are reproducibly passed from one generation to the next generation of inbred plants of the same variety.

Uptake. Uptake refers to the translocation of a particle, such as a dendrimer, across a cell wall or a cellular membrane, wherein the translocation does not occur solely as a result of momentum imparted to the particle by something other than the cell into which the particle is being uptaken. Non-limiting examples of devices or methods that cause translocation of a particle across a cell wall or a cell membrane solely as a result of momentum imparted to the particle are biolistic, gene gun, microinjection, and/or impalefection technologies.

In a particular embodiment, the invention relates to the application of dendrimer as an option for nano-engineering to develop a payload in order to fashion materials for applications in small molecule, biomolecule delivery, gene delivery, imaging, and various biotechnological diagnostics and sensing functions. Dendrimer architecture provides a number of distinctive properties that differentiate them from other polymers and nanoparticles, such as the gradual stepwise method of synthesis, which can provide a well-defined size and structure with a comparatively low polydispersity index. Additionally, dendrimer chemistry can be adaptable and, thus, facilitate synthesis of a broad range of molecules with different functionality. Use of dendrimers according to particular methods of the present invention facilitates biomolecules and gene delivery through use of a high density of terminal groups.

In other embodiments of the invention, multiple attachment sites or filling of an "added" or "guest" molecule may be engineered on the dendrimers at various and/or multiple sites. This property can be employed, for example, in specific targeting and editing of molecular sites within cells for areas such as biomimetics, targeted deliveries, for non-genetically modified organism options, and transient transformation options in a variety of tree or vegetable crops for trait and disease resistance options. Embodiments of the invention can also be employed to develop suitable bio-sensors. In addition, artificial chromosomes (ACES) may be employed with the methods of the invention as an alternative to current eukaryotic vectors for precise targeting and homologous recombination options.

According to embodiments of the invention, there may be provided a method of introducing a molecule of interest into a plant cell comprising a cell wall, the method comprising placing a dendrimer containing a molecule of interest in contact with the plant cell and allowing uptake of the dendrimer across the plant cell wall. In particular aspects of invention, the dendrimer may be any dendrimer and may reversibly or irreversibly contain, may interact with, or otherwise be bound to and/or carry a molecule of interest. In certain embodiments, a molecule of interest may be introduced to the dendrimer before contact with a plant cell having a cell wall or concurrently with the introduction of the dendrimer to a plant cell having a cell wall.

According to embodiments of the present invention, a plant cell having a cell wall may be any plant cell comprising an intact and whole cell wall. Examples of cells having a cell wall include, but are not limited to, algal, tobacco, carrot, maize, canola, rapeseed, cotton, palm, peanut, soybean, sugarcane, *Oryza* sp., *Arabidopsis* sp., and *Ricinus* sp., preferably tobacco, carrots, maize, cotton, canola, soybean and sugarcane; more preferably tobacco and carrots. Embodiments of the invention may include cells comprising a cell wall from any tissue or wherever they are found including, but not limited to, in embryos, meristematic cells, calli, pollen, leaves, anthers, roots, root tips, flowers, seeds, pods, stems, and tissue culture.

In embodiments of the invention, a molecule of interest may be any molecule that can be delivered to a plant cell according to the present invention. Molecules of interest, or components of molecules of interest, may comprise, but are not limited to, nucleic acids, DNA, RNA, RNAi molecules, genes, plasmids, cosmids, YACs, BACs, Plant Artificial Chromosomes, Plant Mini-chromosomes, Plant Engineered Trait Loci DNA; polypeptides, enzymes, hormones, glyco-peptides, sugars, fats, signaling peptides, antibodies, vitamins, messengers, second messengers, amino acids, cAMP, drugs, herbicides, fungicides, antibiotics, and/or combinations thereof.

Embodiments of the invention include methods for the prevention or treatment of disease. Non-limiting example embodiments include the delivery of fungicides, antibiotics, and/or other drugs to cells in need thereof using methods of the present invention.

In aspects of the invention, the dendrimer may be uptaken into various parts of cells. Examples of locations that a dendrimer may be uptaken into include, but are not limited to, cytosol, nucleus, tonoplasts, plastids, etioplasts, chromoplasts, leucoplasts, elaioplasts, proteinoplasts, amyloplasts, chloroplasts, and a lumen of a double membrane. In other embodiments of the invention, dendrimer uptake into a cell comprising a cell wall may occur via the symplastic or apoplastic pathway.

Additional embodiments of the invention include genetically modified plant cells and methods for generating them, wherein the plant cells have one or more nucleic acids introduced therein via methods of the present invention. In one example of an embodiment, a plasmid comprising a gene of interest and a selectable marker may be introduced into a plant cell having a cell well via a dendrimer according to the present invention. In further embodiments, stable transformants may be selected that have stably integrated the gene of interest and/or the selectable marker. In alternative embodiments, a plant cell now comprising the gene of interest may be propagated to produce other cells comprising a molecule of interest. In other embodiments, plant cells now comprising a molecule of interest may be a regenerable cell that may be used to regenerate a whole plant including the molecule of interest.

In another aspect, the present invention provides methods of creating regenerable plant cells comprising a molecule of interest for use in tissue culture. The tissue culture will preferably be capable of regenerating plants having substantially the same genotype as the regenerable cells. The regenerable cells in such tissue cultures can be embryos, protoplasts, meristematic cells, calli, pollen, leaves, anthers, roots, root tips, flowers, seeds, pods or stems. Still further, an embodiment of the invention provides plants regenerated from the tissue cultures of the invention.

Alternatively, the present invention provides a method of introducing a desired trait into a plant cell having a cell wall, wherein the method comprises: placing a dendrimer and a molecule of interest capable of providing the desired trait to the plant cell in contact with the plant cell and allowing uptake of the dendrimer across the cell wall. Examples of desired traits include, but are not limited to, traits selected from male sterility, herbicide resistance, insect resistance, and resistance to bacterial disease, fungal disease, and/or viral disease.

Further aspects of the invention provide for methods of generating stabilized plant lines comprising a desired trait or molecule of interest, wherein the desired trait or molecule of interest may be first introduced by uptake of a dendrimer across a plant cell wall. Methods of generating stabilized plant lines are well known to one of ordinary skill in the art and may include techniques such as, but not limited to, selfing, backcrosses, hybrid production, crosses to populations, and the like. All plants and plant cells comprising a desired trait or molecule of interest first introduced into the plant cell (or its predecessors) by uptake of a dendrimer across a cell wall are within the scope of this invention. Advantageously, the plant cells comprising a desired trait or molecule of interest first introduced into the plant or cell (or its predecessors) by uptake of a dendrimer across a cell wall can be used in crosses with other, different, plant cells to produce first generation ($F_1$) hybrid cells, seeds, and/or plants with superior characteristics.

In embodiments wherein the molecule of interest comprises one or more gene(s), the gene(s) may be a dominant or recessive allele. By way of example, the gene(s) will confer such traits as herbicide resistance, insect resistance, resistance for bacterial resistance, fungal resistance, viral disease resistance, male fertility, male sterility, enhanced nutritional quality, and industrial usage.

With the advent of molecular biological techniques that have allowed the isolation and characterization of genes that encode specific protein or RNA products (e.g., RNAi), scientists in the field of plant biology developed a strong interest in engineering the genome of cells to contain and express foreign genes, or additional or modified versions of native or endogenous genes (perhaps driven by different promoters) in order to alter the traits of a cell in a specific manner. Such foreign additional and/or modified genes are referred to herein collectively as "transgenes." Over the last fifteen to twenty years, several methods for producing transgenic cells have been developed and, in particular embodiments, the present invention relates to transformed versions of cells and methods of producing them via introducing into a cell having a cell wall a transgene via uptake of a dendrimer across a cell wall. In embodiments of the invention, the transgene may be contained in an expression vector.

Cell transformation may involve the construction of an expression vector which will function in a particular cell. Such a vector may comprise DNA that includes a gene under control of or operatively linked to, a regulatory element (for example, a promoter). The expression vector may contain one or more such operably linked gene/regulatory element combinations. The vector(s) may be in the form of a plasmid and can be used alone or in combination with other plasmids to provide transformed cells using transformation methods as described herein to incorporate transgene(s) into the genetic material of a plant cell comprising a cell wall.

In particular embodiments of the invention, a multipurpose STARBURST® PAMAM (polyamidoamine) dendrimer prototype exhibits properties suitable to be used as: (i) targeted, diagnostic MRI (magnetic resonance imaging) INIR (near-IR) contrast agents, (ii) and/or for controlled delivery of cancer therapies. Among them, a lead candidate is [core: 1,4-diaminobutane; G (generation) [PAMAM(CO(2)Na)(64)]. This dendritic nanostructure (i.e., ~5.0 nm diameter) was selected on the basis of a very favorable biocompatibility profile. The Nanotechnology Characterization Laboratory (NCL), an affiliate of the National Cancer Institute (NCI), has completed extensive in vitro studies on the lead compound and have found it to be very benign and highly biocompatible, the expectation being that it will exhibit desirable mammalian kidney excretion properties and demonstrated targeting features. Dendrimers used with the methods of the invention represent a class of polymers characterized by their well-defined structure, with a high degree of molecular uniformity and low polydispersity. In addition, these dendrimers have been shown to be capable of bypassing efflux transporters.

Use of dendrimers according to methods of the present invention has produced stably transformed plants and demonstrated the expression of the stably transformed herbicide gene with the phenotype where high herbicide tolerance was rendered into the transgenic $T_1$ plant. This plant was shown to be fertile as it produced $T_2$ seeds.

In a particular embodiment, SUPERFECT® Transfection Reagent was used. This reagent is a polycation having a defined shape and diameter, available as Qiagen's SUPERFECT® reagent (Qiagen Catalog #301307) as a solution of specifically designed activated dendrimers. Dendrimers are spherical polyamidoamine molecules with branches radiating from a central core and terminating at charged amino groups. Chemical activation promotes efficient uptake of DNA by eukaryotic cells. While not being limited to a particular theory, this reagent is thought to assemble DNA into compact structures, thereby optimizing the entry of DNA into cells. To stabilize the SUPERFECT®-DNA complexes during their transport to the nucleus, the SUPERFECT® reagent is designed to buffer the lysosome after fusion with the endosome, leading to pH inhibition of lysosomal nucleases.

Expression Vectors for Uptake via Dendrimer: Marker Genes

Expression vectors may include at least one genetic marker, operably linked to a regulatory element (a promoter, for example) that allows transformed cells containing the marker to be either recovered by negative selection (i.e., inhibiting growth of cells that do not contain the selectable marker gene) or by positive selection (i.e., screening for the product encoded by the genetic marker). Many selectable marker genes for transformation are well-known in the transformation arts and include, for example, genes that code for enzymes that metabolically detoxify a selective chemical agent that may be an antibiotic or an herbicide, or genes that encode an altered target, which may be insensitive to the inhibitor. A few positive selection methods are also known in the art.

One commonly used selectable marker gene suitable for plant transformation may include the neomycin phosphotransferase II (nptII) gene under the control of plant regulatory signals, which confers resistance to kanamycin. See, e.g., Fraley et al., *Proc. Natl. Acad. Sci. U.S.A.* 80:4803 (1983). Another commonly used selectable marker gene may be the hygromycin phosphotransferase gene, which confers resistance to the antibiotic hygromycin. See, e.g., Van den Elzen et al., *Plant Mol. Biol.* 5:299 (1985).

Additional selectable marker genes of bacterial origin that confer resistance to antibiotics include gentamycin acetyl transferase, streptomycin phosphotransferase, aminoglycoside-3'-adenyl transferase, and the bleomycin resistance determinant. See Hayford et al., *Plant Physiol.* 86:1216 (1988); Jones et al., *Mol. Gen. Genet.* 210:86 (1987); Svab et al., *Plant Mol. Biol.* 14:197 (1990); Hille et al., *Plant Mol. Biol.* 7:171 (1986). Other selectable marker genes confer resistance to herbicides such as glyphosate, glufosinate or bromoxynil. See Comai et al., *Nature* 317:741-744 (1985); Gordon-Kamm et al., *Plant Cell* 2:603-618 (1990); and Stalker et al., *Science* 242:419-423 (1988).

Other selectable marker genes suitable for plant transformation are not of bacterial origin. These genes include, for example, mouse dihydrofolate reductase, plant 5-enolpyruvylshikimate-3-phosphate synthase and plant acetolactate synthase. See Eichholtz et al., Somatic Cell Mol. Genet. 13:67 (1987); Shah et al., *Science* 233:478 (1986); Charest et al., *Plant Cell Rep.* 8:643 (1990).

Another class of marker genes suitable for plant transformation requires screening of presumptively transformed plant cells rather than direct genetic selection of transformed cells for resistance to a toxic substance, such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening transformed cells include β-glucuronidase (GUS), β-galactosidase, luciferase and chloramphenicol acetyltransferase. See Jefferson, R. A., *Plant Mol. Biol. Rep.* 5:387 (1987); Teeri et al., *EMBO J.* 8:343 (1989); Koncz et al., *Proc. Natl. Acad. Sci. U.S.A.* 84:131 (1987); DeBlock et al., *EMBO J.* 3:1681 (1984).

Recently, in vivo methods for visualizing GUS activity that do not require destruction of plant tissue have been made available. Molecular Probes publication 2908, IMAGENE GREEN™, pp. 1-4 (1993); and Naleway et al., *J. Cell Biol.* 115:151a (1991). However, these in vivo methods for visualizing GUS activity have not proven useful for recovery of transformed cells because of low sensitivity, high fluorescent backgrounds, and limitations associated with the use of luciferase genes as selectable markers.

More recently, genes encoding Fluorescent Proteins (e.g., GFP, EGFP, EBFP, ECFP, and YFP) have been utilized as markers for gene expression in prokaryotic and eukaryotic cells. See Chalfie et al., *Science* 263:802 (1994). Fluorescent proteins and mutations of fluorescent proteins may be used as screenable markers.

Expression Vectors for Uptake Via Dendrimer: Promoters

Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA that may be upstream from the start of transcription and that may be involved in recognition and binding of RNA polymerase and other proteins to initiate transcription. A "plant promoter" may be a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in certain tissues are referred to as "tissue-specific." A "cell type" specific promoter primarily drives expression in certain cell types in one or more organs, for example, vascular cells in roots or leaves. An "inducible" promoter may be a promoter that may be under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter may be a promoter that may be active under most environmental conditions.

A. Inducible Promoters

An inducible promoter may be operably linked to a gene for expression in a cell. Optionally, the inducible promoter may be operably linked to a nucleotide sequence encoding a signal sequence, which may be operably linked to a gene for expression in a cell. With an inducible promoter, the rate of transcription increases in response to an inducing agent.

Any inducible promoter can be used in the instant invention. See Ward et al., *Plant Mol. Biol.* 22:361-366 (1993). Exemplary inducible promoters include, but are not limited to: those from the ACEI system that responds to copper (Mett et al., *PNAS* 90:4567-4571 (1993)); In2 gene from maize that responds to benzenesulfonamide herbicide safeners (Hershey et al., *Mol. Gen. Genetics* 227:229-237 (1991); and Gatz et al., *Mol. Gen. Genetics* 243:32-38 (1994)); and Tet repressor from Tn10 (Gatz et al., *Mol. Gen. Genetics* 227:229-237 (1991)). A particularly useful inducible promoter may be a promoter that responds to an inducing agent to which plants do not normally respond. An exemplary inducible promoter may be the inducible promoter from a steroid hormone gene, the transcriptional activity of which may be induced by a glucocorticosteroid hormone. Schena et al., *Proc. Natl. Acad. Sci. U.S.A.* 88:0421 (1991).

B. Constitutive Promoters

A constitutive promoter may be operably linked to a gene for expression in a cell or the constitutive promoter may be operably linked to a nucleotide sequence encoding a signal sequence, which may be operably linked to a gene for expression in a cell.

Different constitutive promoters can be utilized in the instant invention. Exemplary constitutive promoters include, but are not limited to: promoters from plant viruses, such as the 35S promoter from CaMV (Odell et al., *Nature* 313:810-812 (1985)); promoters from rice actin genes (McElroy et al., *Plant Cell* 2:163-171 (1990)); ubiquitin (Christensen et al., *Plant Mol. Biol.* 12:619-632 (1989); and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)); and maize H3 histone (Lepetit et al., *Mol. Gen. Genetics* 231:276-285 (1992); and Atanassova et al., *Plant Journal* 2 (3):291-300 (1992)). The ALS promoter, Xba1/NcoI fragment 5' to the *Brassica napus* ALS3 structural gene (or a nucleotide sequence similarity to said Xba1/NcoI fragment), represents a particularly useful constitutive promoter. See PCT application WO 96/30530.

C. Tissue-Specific or Tissue-Preferred Promoters

A tissue-specific promoter may be operably linked to a gene for expression in a cell. Optionally, the tissue-specific promoter may be operably linked to a nucleotide sequence encoding a signal sequence which may be operably linked to a gene for expression in a cell. Plants transformed with a gene of interest operably linked to a tissue-specific promoter can produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23:476-482 (1983); and Sengupta-Gopalan et al., *Proc. Natl. Acad. Sci. U.S.A.* 82:3320-3324 (1985)); a leaf-specific and light-induced promoter such as that from cab or rubisco (Simpson et al., *EMBO J.* 4(11): 2723-2729 (1985); and Timko et al., Nature 318:579-582 (1985)); an anther-specific promoter such as that from LAT52 (Twell et al., *Mol. Gen. Genetics* 217:240-245 (1989)); a pollen-specific promoter such as that from Zm13 (Guerrero et al., *Mol. Gen. Genetics* 244:161-168 (1993)) or a microspore-preferred promoter such as that from apg (Twell et al., *Sex. Plant Reprod.* 6:217-224 (1993)).

Transport of protein produced by transgenes to a subcellular compartment, such as the chloroplast, vacuole, peroxisome, glyoxysome, cell wall or mitochondrion, or for secretion into the apoplast, can be accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein may be ultimately compartmentalized. Alternatively, such subcellular compartment targeting proteins can be directly linked to a dendrimer to direct the dendrimer coated with the molecule of interest to the desired subcellular compartment.

The presence of a signal sequence directs a polypeptide to either an intracellular organelle or subcellular compartment, or for secretion to the apoplast. Many signal sequences are known in the art. See, e.g., Becker et al., *Plant Mol. Biol.* 20:49 (1992); P. S. Close, Master's Thesis, Iowa State University (1993); C. Knox et al., "Structure and Organization of Two Divergent Alpha-Amylase Genes from Barley," *Plant Mol. Biol.* 9:3-17 (1987); Lerner et al., *Plant Physiol.* 91:124-129 (1989); Fontes et al., *Plant Cell* 3:483-496 (1991); Matsuoka et al., *Proc. Natl. Acad. Sci.* 88:834 (1991); Gould et al., *J. Cell Biol.* 108:1657 (1989); Creissen et al., *Plant* 1 2:129 (1991); Kalderon et al., A short amino acid sequence able to specify nuclear location, *Cell* 39:499-509 (1984); Steifel et al., Expression of a maize cell wall hydroxyproline-rich glycoprotein gene in early leaf and root vascular differentiation, *Plant Cell* 2:785-793 (1990).

Foreign Protein Genes and Agronomic Genes

With transgenic plants, according to the present invention, a foreign protein can be produced in commercial quantities. Thus, techniques for the selection and propagation of transformed plants, which are well understood in the art, yield a plurality of transgenic plants that are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-96 (1981).

In aspects of the invention, the transgenic plant provided for commercial production of foreign protein may be a cell or a plant. In other aspects, the biomass of interest may be seed. For the relatively small number of transgenic plants that show higher levels of expression, a genetic map can be generated primarily via conventional RFLP (Restriction Fragment Length Polymorphism), PCR (Polymerase Chain Reaction) and SSR (Short Sequence Repeat) analysis, which identifies the approximate chromosomal location of the integrated DNA molecule. For exemplary methodologies in this regard, see Glick and Thompson, *Methods in Plant Molecular Biology and Biotechnology* CRC Press, Boca Raton 269:284 (1993). Map information concerning chromosomal location may be useful for proprietary protection of a subject transgenic plant. If unauthorized propagation may be undertaken and crosses are made with other germplasm, the map of the integration region can be compared to similar maps for suspect plants to determine if the latter have a common parentage with the subject plant. Map comparisons would involve hybridizations, RFLP, PCR, SSR and sequencing, all of which are conventional techniques.

Likewise, agronomic genes can be expressed in transformed cells or their progeny. More particularly, plants can be genetically engineered via the methods of the invention to express various phenotypes of agronomic interest. Exemplary genes that may be used in this regard include, but are not limited to, those categorized below.

1. Genes that Confer Resistance to Pests or Disease and that Encode:

A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance genes to engineer plants that are resistant to specific pathogen strains. See, e.g., Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. tomato encodes a protein kinase); Mindrinos et al., *Cell* 78:1089 (1994) (Arabidopsis may be RSP2 gene for resistance to *Pseudomonas syringae*).

B) A gene conferring resistance to a pest, such as soybean cyst nematode. See, e.g., PCT Application WO 96/30517; PCT Application WO 93/19181.

C) A *Bacillus thuringiensis* protein, a derivative thereof or a synthetic polypeptide modeled thereon. See, e.g., Geiser et al., *Gene* 48:109 (1986), which discloses the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

D) A lectin. See, for example, the disclosure by van Damme et al., *Plant Molec. Biol.* 24:25 (1994), who disclose the nucleotide sequences of several *Clivia miniata* mannose-binding lectin genes.

E) A vitamin-binding protein, such as avidin. See PCT application U.S. 93/06487. The application teaches the use of avidin and avidin homologues as larvicides against insect pests.

F) An enzyme inhibitor, for example, a protease or proteinase inhibitor or an amylase inhibitor. See, e.g., Abe et al., *J. Biol. Chem.* 262:16793 (1987) (nucleotide sequence of rice cysteine proteinase inhibitor); Huub et al., *Plant Molec. Biol.* 21:985 (1993) (nucleotide sequence of cDNA encoding tobacco proteinase inhibitor I); Sumitani et al., *Biosci. Biotech. Biochem.* 57:1243 (1993) (nucleotide sequence of *Streptomyces nitrosporeus* α-amylase inhibitor) and U.S. Pat. No. 5,494,813 (Hepher and Atkinson, issued Feb. 27, 1996).

G) An insect-specific hormone or pheromone such as an ecdysteroid or juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

H) An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor); and Pratt et al., *Biochem. Biophys. Res. Comm.* 163:1243 (1989) (an allostatin may be identified in *Diploptera puntata*). See also U.S. Pat. No. 5,266,317 to Tomalski et al., which discloses genes encoding insect-specific, paralytic neurotoxins I) An insect-specific venom produced in nature by a snake, a wasp, or any other organism. For example, see Pang et al., *Gene* 116:165 (1992), for disclosure of heterologous expression in plants of a gene coding for a scorpion insectotoxic peptide.

J) An enzyme responsible for a hyperaccumulation of a monoterpene, a sesquiterpene, a steroid, hydroxamic acid, a phenylpropanoid derivative or another non-protein molecule with insecticidal activity.

K) An enzyme involved in the modification, including the post-translational modification, of a biologically active molecule, for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules that contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hornworm chitinase; and Kawalleck et al., *Plant Molec. Biol.* 21:673 (1993), who provide the nucleotide sequence of the parsley ubi4-2 polyubiquitin gene.

L) A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

M) A hydrophobic moment peptide. See PCT application WO 95/16776 (disclosure of peptide derivatives of Tachyplesin, which inhibit fungal plant pathogens) and PCT application WO 95/18855 (teaches synthetic antimicrobial peptides that confer disease resistance).

N) A membrane permease, a channel former or a channel blocker. For example, see the disclosure of Jaynes et al., *Plant Sci.* 89:43 (1993), of heterologous expression of a cecropin-13 lytic peptide analog to render transgenic tobacco plants resistant to *Pseudomonas solanacearum*.

O) A viral-invasive protein or a complex toxin derived therefrom. For example, the accumulation of viral coat proteins in transformed plant cells imparts resistance to viral infection and/or disease development effected by the virus from which the coat protein gene may be derived, as well as by related viruses. See Beachy et al., *Ann. Rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

P) An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Intl Symposium on Molecular Plant-Microbe Interactions (Edinburgh, Scotland) (1994) (enzymatic inactivation in transgenic tobacco via production of single-chain antibody fragments).

Q) A virus-specific antibody. See, for example, Tavladoraki et al., *Nature* 366:469 (1993), who show that transgenic plants expressing recombinant antibody genes are protected from virus attack.

R) A developmental-arrestive protein produced in nature by a pathogen or a parasite. For example, fungal endo α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene that encodes a bean endopolygalacturonase-inhibiting protein may be described by Toubart et al., *Plant J.* 2:367 (1992).

S) A developmental-arrestive protein produced in nature by a plant. For example, Logemann et al., *Bio/Technology* 10:305 (1992), have shown that transgenic plants expressing the barley ribosome-inactivating gene have an increased resistance to fungal disease.

2. Genes that Confer Resistance to an Herbicide:

A) An herbicide that inhibits the growing point or meristem, such as an imidazolinone, a sulfonamide, or a sulfonylurea. Exemplary genes in this category code for mutant ALS and AHAS enzyme as described, for example, by Lee et al., *EMBO J.* 7:1241 (1988), and Mild et al., *Theor. Appl. Genet.* 80:449 (1990), respectively.

B) Glyphosate (resistance conferred by, e.g., mutant 5-enolpyruvylshikimate-3-phosphate synthase (EPSPs) genes (via the introduction of recombinant nucleic acids and/or various forms of in vivo mutagenesis of native EPSPs genes), aroA genes and glyphosate acetyl transferase (GAT) genes, respectively), other phosphono compounds such as glufosinate (phosphinothricin acetyl transferase (PAT) genes from *Streptomyces* species, including *Streptomyces hygroscopicus* and *Streptomyces viridichromogenes*), and pyridinoxy or phenoxy proprionic acids and cyclohexones (ACCase inhibitor-encoding genes), See, for example, U.S. Pat. No. 4,940,835 to Shah et al. and U.S. Pat. No. 6,248,876 to Barry et. al., which disclose nucleotide sequences of forms of EPSPs that can confer glyphosate resistance to a plant. A DNA molecule encoding a mutant aroA gene can be obtained under ATCC accession number 39256, and the nucleotide sequence of the mutant gene may be disclosed in U.S. Pat. No. 4,769,061 to Comai. European Patent Application No. 0 333 033 to Kumada et al., and U.S. Pat. No. 4,975,374 to Goodman et al., disclose nucleotide sequences of glutamine synthetase genes, which confer resistance to herbicides such as L-phosphinothricin. The nucleotide sequence of a PAT gene may be provided in European Patent Application No. 0 242 246 to Leemans et al., while DeGreef et al., *Bio/Technology* 7:61 (1989), describe the production of transgenic plants that express chimeric bar genes coding for PAT activity. Exemplary of genes conferring resistance to phenoxy proprionic acids and cyclohexones, such as sethoxydim and haloxyfop include the Acc1-S1, Acc1-S2 and Acc1-S3 genes described by Marshall et al., *Theor. Appl. Genet.* 83:435 (1992). GAT genes capable of conferring glyphosate resistance are described in WO 2005/012515 to Castle et al. Genes conferring resistance to 2,4-D, phenoxyproprionic acid and pyridyloxy auxin herbicides are described in WO 2005/107437 assigned to Dow AgroSciences LLC.

C) An herbicide that inhibits photosynthesis, such as a triazine (psbA and gs+ genes) or a benzonitrile (nitrilase gene). Przibila et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase may be described by Hayes et al., *Biochem. J.* 285:173 (1992).

3. Genes that Confer or Contribute to a Value-Added Trait, Such as:

A) Modified fatty acid metabolism, for example, by transforming a plant with an antisense gene of stearyl-ACP desaturase to increase stearic acid content of the plant. See Knultzon et al., *Proc. Natl. Acad. Sci. U.S.A.* 89:2624 (1992).

B) Decreased phytate content—1) Introduction of a phytase-encoding gene would enhance breakdown of phytate, adding more free phosphate to the transformed plant. For example, see van Hartingsveldt et al., *Gene* 127:87 (1993), for a disclosure of the nucleotide sequence of an *Aspergillus niger* phytase gene. 2) A gene could be introduced that reduced phytate content. In maize, for example, this could be accomplished by cloning and then reintroducing DNA associated with the single allele that may be responsible for maize mutants characterized by low levels of phytic acid. See Raboy et al., *Maydica* 35:383 (1990).

C) Modified carbohydrate composition effected, for example, by transforming plants with a gene coding for an enzyme that alters the branching pattern of starch. See Shiroza et al., *J. Bacteria* 170:810 (1988) (nucleotide sequence of *Streptococcus mutants* fructosyltransferase gene); Steinmetz et al., *Mol. Gen. Genet.* 20:220 (1985) (nucleotide sequence of *Bacillus subtilis* may be levansucrase gene); Pen et al., *Bio/Technology* 10:292 (1992) (production of transgenic plants that express *Bacillus licheniformis* may be α-amylase); Elliot et al., *Plant Molec. Biol.* 21:515 (1993) (nucleotide sequences of tomato invertase genes); Søgaard et al., *J. Biol. Chem.* 268:22480 (1993) (site-directed mutagenes may be of barley α-amylase gene); and Fisher et al., *Plant Physiol.* 102:1045 (1993) (maize endosperm starch branching enzyme II).

EXAMPLES

The present invention is further described in the following examples, which are offered by way of illustration and are not intended to limit the invention in any manner.

Example 1

Preparation of Dendrimer/DNA Complex and Treatment of Cells 1.1 Preparation of Plasmid pDAB3831 plasmid DNA (FIG. 1) (SEQ ID NOs:1 and 2) was isolated and prepared for dendrimer-mediated plant transformation. Transformation experiments were tested using both circularized DNA and linearized DNA.

To linearize pDAB3831, a PCR reaction was completed. pDAB3831 was PCR amplified using a continuous thermal cycling system, which has been described previously in, for example, WO 2008/045288. Rather than using small tubes, continuous thermal cyclers use a constant or continuous stream of fluid repetitively passed through different temperature zones to amplify DNA. PCR reaction mixture was injected into a carrier fluid with which the PCR reaction mixture is immiscible. The carrier fluid was then passed through a plurality of temperature zones to facilitate DNA amplification within the PCR reaction mixture. A sample was prepared containing: 12% $MgCl_2$ (25 mM), 0.33% Taq DNA polymerase (5 units/µl), 2.0% dNTPs (deoxyadenosine triphosphate (dATP), deoxycytidine triphosphate (dCTP), deoxyguanosine triphosphate (dGTP) and deothythimidine triphosphate (dTTP), 8.0% template (2 µg/ml), 61.66% PLURONIC® F108 solution (1.5% solution), 4% forward primer, 4% reverse primer, and 8% reaction buffer (10× concentration). The adjacent sectors of the system were set at a temperature of 95° C., 59° C. and 72° C. for dissociation, annealing and extension purposes, respectively. The PCR reaction mixture was pumped through the system using a pressurized vessel at 13.79 $N/cm^2$. After the reaction mixture was fed to the temperature control body, mineral oil was used to push the sample through the entire length of tubing. The flow rate of the reaction mixture was controlled with a flow valve to 0.25 ml/min. The specific DNA sequence present in the sample was amplified as it passed cyclically through the temperature zones. After the thirtieth cycle, the contents were collected. PCR product was purified on a gel filtration column followed by ethanol precipitation. A sample of the purified product was analyzed on an Agilent Bioanalyzer, as well as agarose gel electrophoresis to confirm the size and the concentration of the PCR product.

The template used for the PCR described above was DAS plasmid pDAB3831, which contains the PAT selectable marker gene driven by the *Arabidopsis* ubiquitin 10 promoter (AtUbi10) and the *Philadium* Yellow Fluorescence Protein gene (PhiYFP) driven by the Cassaya Vein Mosaic Virus promoter (CsVMV). Forward primer SEQ ID NO:3 and reverse primer SEQ ID NO:4 were synthesized to amplify the 4.6 kbp complete expression cassette (i.e., the linearized DNA) containing both genes and their promoters. In addition, to facilitate the conjugation of the linear dsDNA to the surface of the nanoparticles, a biotin molecule was chemically linked to the phosphate group of the primers using Biotin-TEG-CE-phosphoramidite. This phosphoramidite has an extended 15-atom mixed polarity spacer arm based on a triethylene glycol linker. This extended spacer arm can separate the biotin function from the rest of an oligo to advantageously reduce any possible steric hindrance effects during binding to the streptavidin molecule. When the forward primer was labeled, the biotin was at the beginning of the DNA. When the reverse primer was labeled, the biotin was at the end of the DNA fragment. The biotinylated (both orientations) DNA fragment can therefore be attached to streptavidin coated nanoparticles. Using the biotinylated oligos and the continuous thermal cycling system, approximately 20 mg of the linear DNA fragment was produced.

1.2 Preparation of the DNA/Dendrimer Complex

The dendrimers used for these experiments were spherical cationic polyamidoamine (PAMAM) cascade polymers that consist of primary amines on the surface and tertiary amines in the interior. The dendrimers are partially degraded by heat treatment in solvolytic solvents, thereby resulting in less sterical constraint and greater flexibility. The dendrimer's highly positive charge facilitates electrostatic interactions with DNA, and the flexible structure allows the dendrimer to compact when bound to DNA and swell when released from the DNA. The transfection or transformation efficiency is increased as a result of the positive charge and the flexible structural property of the dendrimer.

Dendrimers were obtained from Qiagen (Germantown, Md.), which are marketed as SUPERFECT® Transfection Reagent (Cat #301305). The plasmid DNA was mixed with 0.6 ml of SUPERFECT® reagent and incubated for 30 minutes at 24° C. to form a DNA/Dendrimer complex. Varying concentrations of circularized plasmid DNA (0.1 mg and 0.5 mg) were used to four the DNA/Dendrimer complex. In addition, the linearized DNA described above in Example 1.1 was used to form a DNA/Dendrimer complex. Concentrations of 0.1 mg and 0.5 mg of linear DNA were used. After formation of the DNA/Dendrimer complex, a 10 ml volume solution containing 5% sucrose and 0.02-0.04% SILWET-L77® was added to the DNA/Dendrimer reaction.

Example 2

DNA/Dendrimer Complex Delivery and Stable Transformation of *Arabidopsis Thaliana*

2.1 Plant Material for in Planta Transformation:

Synchronized germination of the seed is important to ensure the uniformity of floral development in the $T_0$ plants. *Arabidopsis thaliana* cv. Columbia seed was suspended in 0.1% agar solution and incubated at 4° C. for 48 hours to complete stratification. Sixty mg of seed was weighed and transferred to a 15 ml tube. Thirteen ml of 0.1% agar solution was added and was vortexed until seed was evenly dispersed. This created a concentration of 4.6 mg seed/1 ml solution (or about 230 seeds/10. Six tubes (72 ml solution) were prepared to sow four flats that contained 18 (3½-inch) pots in each tray.

The solution was incubated at 4° C. for 48 hours to complete stratification. Each pot was sown individually at 1.0 ml of stratified seed solution per pot. When all the pots were sown, propagation domes were placed on the trays to keep the soil moist. The domes were removed five days after the sow date. Seeds were germinated and plants were grown in a CONVIRON® (models CMP4030 and CMP3244, Controlled Environments Limited, Winnipeg, Manitoba, Canada) under long day conditions (16-hours light/8-hours dark) at a light intensity of 120-150 $\mu$mol/m$^2$sec under constant temperature (22° C.) and humidity (40% to 50%). Plants were watered 10 to 14 days after sowing the plants with Hoagland's solution and, subsequently, with DI water to keep the soil moist but not wet. After four weeks post-sow date, the flowers were cut back to produce a more even growth of secondary flowers. In the fifth week post-sowing, the plants were prepared for the transformation process.

2.2 In Planta Transformation and Screening $T_1$ Resistant Plants:

Dendrimer-mediated transformation of *Arabidopsis thaliana* cv. Columbia was completed using a modified protocol from Clough and Bent. (S. J. Clough and A. F. Bent, 1998, *Plant J.* 16:735-43). A 10 ml suspension was made with the DNA/Dendrimer solution and used for treatments of the *Arabidopsis* plants (mostly immature flower clusters with some fertilized siliques). Both circular DNA/Dendrimer complexes and linear DNA/Dendrimer complexes were used independent of one another. Before dipping plants, SILWET L-778 to a concentration of 0.05% (250 ul/500 ml)-0.005% was added to the DNA/Dendrimer solution and mixed well. Above-ground parts of plant were dipped in the DNA/Dendrimer solution for 2-30 seconds, with gentle agitation. Treated plants were kept under a plastic dome cover for 16-24 hours at 22° C. to 24° C. The plants were transferred to the CONVIRONS® and allowed to grow to maturity and to grow seeds. Selection trays (10.5"×21"×1" trays) were used to screen bulk harvest seed from $T_0$ plants, with approximately 10,000 seeds on each tray. Two controls were used to ensure selection spraying was done correctly: Col-0 negative transformant control and Columbia Col-0 wild-type spiked with homozygous seed for PAT (Phospinothricin acetyl transferase) selectable marker as a positive transformant control. To achieve synchronization, seeds were stratified in a 0.1% agar solution for 48 hours prior to sowing. To provide 10,000 seeds per selection tray, 200 mg of seeds were added to a 0.1% agar solution and vortexed until the seeds were evenly suspended. The stratified seeds were then sowed on selection trays filled with Sunshine Mix LP5 and sub-irrigated with Hoagland's solution. To increase effectiveness of the selection spray, 40 ml of suspended seed was sown evenly onto the selection tray. After sowing propagation domes were placed on each selection tray and plants were grown for selection, propagation domes were removed approximately five days post-sowing.

Additionally, a control experiment was completed wherein a solution containing only DNA, without dendrimers, was used to transform *Arabidopsis thaliana*. The previously described protocol was used for transformation of naked DNA. Both linear and circular forms of DNA were used independent of one another.

Figure 2:
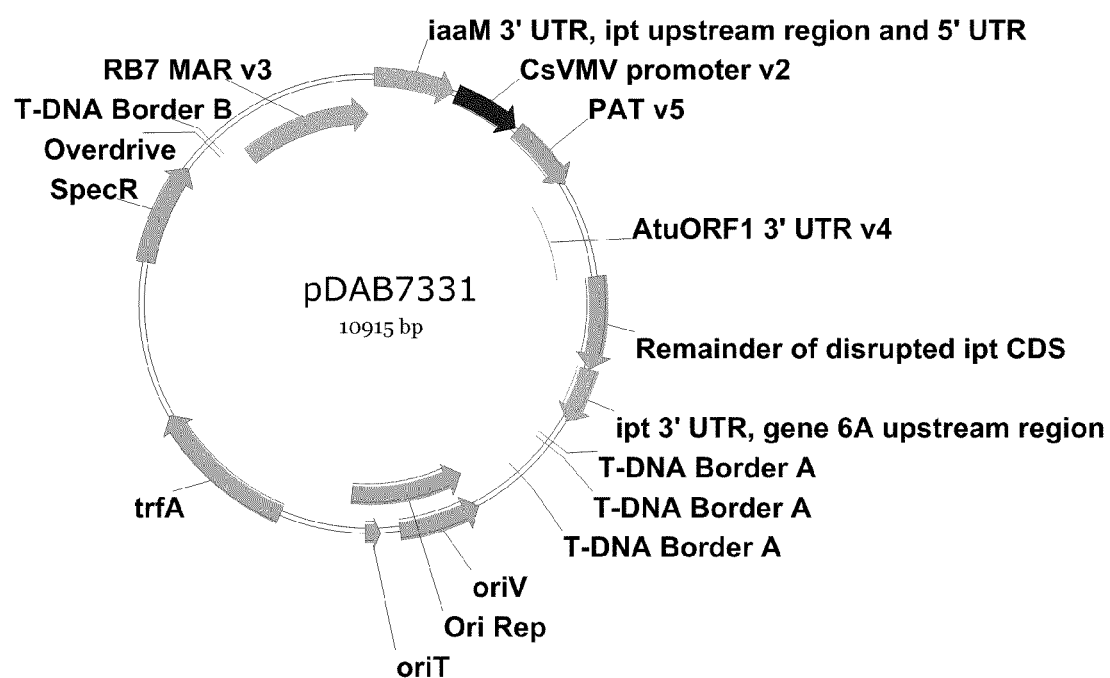
FIG. 2 shows Plasmid pDAB7331.
Figure 3:
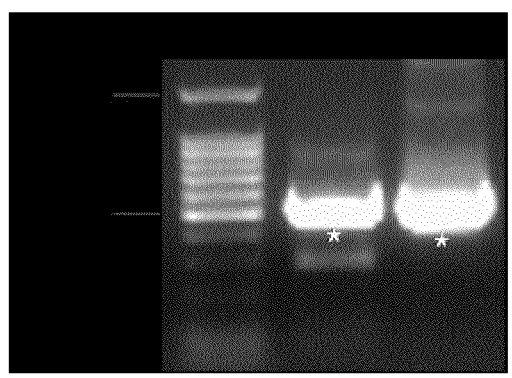
FIG. 3 is an ethidium bromide stained gel image showing PAT PCR amplification from genomic DNA of *Arabidopsis* transgenic plant: 100 DNA ladder (Promega Inc.) 1; *Arabidopsis* transgenic line from SUPERFECT® with pDAB3831 treatment 2; plasmid DNA pDAB3831 as a positive control; asterisks indicate the PAT PCR amplicon.
Figure 4:
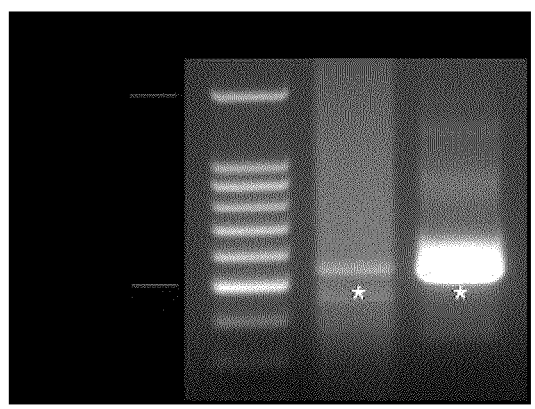
FIG. 4 is a gel image showing YFP PCR amplification from genomic DNA of *Arabidopsis* transgenic plant: 100 DNA ladder (Promega Inc.) 1; *Arabidopsis* transgenic line from SUPERFECT® with pDAB3831 treatment 2; plasmid DNA pDAB3831 as a positive control; asterisks indicate the YFP PCR amplicon.

An additional control transformation for *Arabidopsis thaliana* using *Agrobacterium* was completed. This transformation was used as a benchmark to determine the efficiency of the dendrimer-mediated transformation. The plasmid, pDAB733 I (FIG. 2), was transformed into *Agrobacterium* using a modified protocol from Hanahan (1983), this strain was used for the *Agrobacterium*-mediated transformation of *Arabidopsis thaliana* cv. Columbia.

*Arabidopsis* was transformed using the floral dip method described by Clough and Bent. A selected *Agrobacterium* colony was used to inoculate one or more 100 ml pre-cultures of YEP broth containing spectinomycin (100 mg/L) and kanamycin (50 mg/L). The culture(s) was incubated overnight at 28° C. with constant agitation at 225 rpm. The cells were pelleted at approximately 5000×g for 10 minutes at room temperature, and the resulting supernatant discarded. The cell pellet was gently resuspended in 400 ml dunking media containing: 5% (w/v) sucrose, 10 μg/L 6-benzylaminopurine, and 0.04% SILWET L-77®. Approximately one-month-old plants were dipped into the media for 5-10 minutes with gentle agitation. The plants were laid down on their sides and covered (transparent or opaque) for two to three hours, and then placed upright. The plants were grown at 22° C., with a 16-hour light/8-hour dark photoperiod. Approximately four weeks after dipping, the seeds were harvested.

2.3 Selection of Transformed Plants

Freshly harvested $T_1$ seed were allowed to dry for seven days at room temperature. $T_1$ seed were sown in 26.5×51 cm germination trays, each receiving a 200 mg aliquot of stratified $T_1$ seed (10,000 seed) that had previously been suspended in 40 ml of 0.1% agarose solution and stored at 4° C. for two days to complete dormancy requirements and ensure synchronous seed germination.

Sunshine Mix LP5 was covered with fine vermiculite and subirrigated with Hoagland's solution until wet, then allowed to gravity drain. Each 40 ml aliquot of stratified seed was sown evenly onto the vermiculite with a pipette and covered with humidity domes for four to five days. Domes were removed one day prior to initial transformant selection using glufosinate post-emergence spray.

Seven days after planting (DAP), $T_1$ plants (cotyledon and 2-4-1f stage, respectively) were sprayed five times within five days with a 0.2% solution of LIBERTY® herbicide (200 g ae/L glufosinate, Bayer Crop Sciences, Kansas City, Mo.) at a spray volume of 10 ml/tray (703 L/ha) using a DeVilbiss compressed air spray tip to deliver an effective rate of 280 g ae/ha glufosinate per application. Survivors (plants actively growing) were identified four to seven days after the final spraying and transplanted individually into three-inch pots prepared with potting media (Metro Mix 360). Transplanted plants were covered with humidity domes for three to four days and placed in a 22° C. growth chamber as before or moved directly to a greenhouse. Domes were subsequently removed and plants reared in the greenhouse (22±5° C., 50±30% RH, 14 hours light:10 dark, minimum 500 μE/m$^2$s$^1$ natural+supplemental light).

Example 3

Molecular Analysis of the Genomic Integration of Transgenes in the $T_1$ Progeny of *Arabidopsis Thaliana* Cv Columbia 3.1 gDNA PCR Amplification of Transgenes Genomic DNA from *Arabidopsis* transgenic plants was extracted from total leaf material of six-week-old plants using a Plant DNAZOL® kit according to the manufacturer's instructions. PCR primers were designed for detection of the YFP and PAT transgenes. The YFP primers are represented as SEQ ID NO:5 and SEQ ID NO:6. The PAT primers are represented as SEQ ID NO:7 and SEQ ID NO:8.

Figure 5:
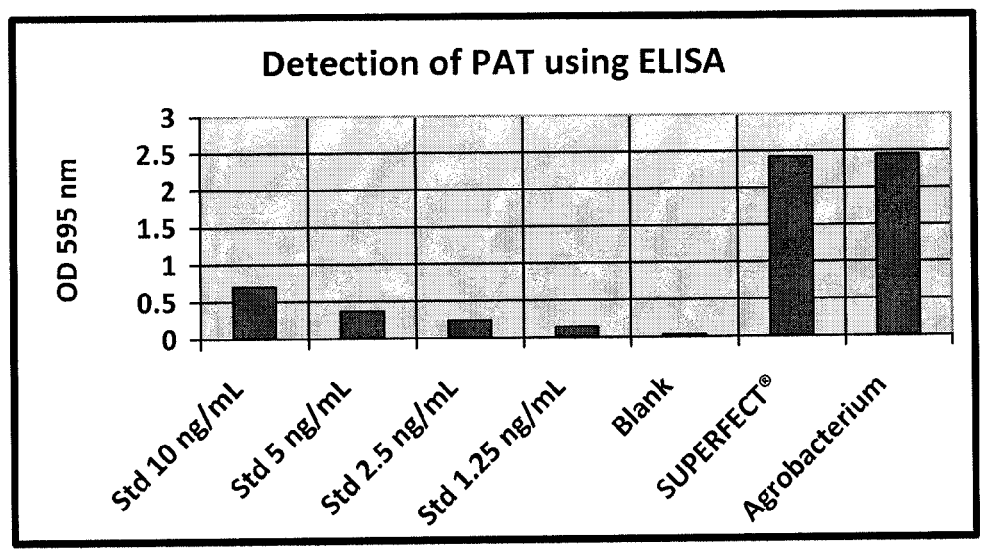
FIG. 5 shows PAT protein expression levels from leaf tissues of dendrimer-mediated (SUPERFECT®) transformed *Arabidopsis* plants; using a commercial ELISA (Enzyme Linked Immuno-sorbent assay) kit, PAT protein was detected in the dendrimer-mediated transgenic plants and compared to plants that were transformed via *Agrobacterium tumefaciens*.

PCR amplification reactions for PAT and YFP were completed using the TaKaRa EXTAQ™ kit (Takara Bio, Otsu, Shiga, Japan). Gene products were amplified in a total reaction volume of 50 μl. The PCR reaction contained 100 ng genomic DNA template, 1×ExTaq reaction buffer, 0.2 mM dNTP, 10 pMol of each primer, and 0.025 units/μL ExTaq. The following PCR conditions were used: 1 cycle at 96° C. for five minutes; and 31 cycles of the following conditions: 94° C. for 15 seconds; 65° C. for 30 seconds; 72° C. for one minute; and a final extension of 72° C. for 7 minutes. PCR amplification product was analyzed by 0.8% TAE agarose gel electrophoresis and visualized by ethidium bromide staining. FIG. 5 shows the amplification products that were obtained from these reactions.

The PCR fragments were sequenced using the PAT forward primer (SEQ ID NO:7) and YFP forward primer (SEQ ID NO:5) using advanced Sanger sequencing technology (MWG Biotech, Huntsville, Ala.). The sequence data was analyzed using SEQUENCHER® software.

The sequencing results of the PAT and YFP PCR amplicons matched the expected nucleotide sequence for these genes. These results indicate that the PAT and YFP sequences from pDAB3831 (FIG. 1) were stably integrated into the gDNA of *Arabidopsis* using the SUPERFECT® Transfection Reagent.

3.2 ELISA Screening of PAT

Protein was extracted from six-week-old transgenic *Arabidopsis* plant leaves for detection of expressed PAT protein via ELISA (enzyme linked immuno-sorbent assay). A microfuge tube containing the leaf samples was chilled in liquid nitrogen. The leaf material was ground to a powder using a disposable homogenizer. After equilibrating on ice for 5 minutes, 200 μl of extraction buffer (PBST; 20 mM phosphate buffered saline containing 0.05% (v/v) TWEEN® 20) was added. The contents were mixed with a vortex and centrifuged at 4° C. for 10 minutes at 13,000×g. Supernatant was extracted from the cell debris and stored on ice until further analysis.

The ELISA was performed using a modified protocol for the QUALIPLATE™ Kit for LIBERTYLINK® PAT/pat- (Envirologix, Portland, Me.). The ELISA plate and other reagents were equilibrated at room temperature. Fifty μl of enzyme conjugate was added to each well of the plate. Another 50 μl of extraction buffer was added to each well of the plate. Serial dilutions of the purified transgenic *Arabidopsis* protein were added to the wells. Concentrations of 10, 5, 2.5, and 1.25 ng/ml were used. Additional standards and plant extracts were added to wells as controls. The plate was shaken at 200 rpm and incubated at room temperature for two hours. After the incubation, the plate was washed five times with extraction buffer in a plate washer. For detection, 100 μl of substrate from the kit was added to each well and the plate was incubated for 30 minutes. Activity was read and recorded using a microplate reader at an absorbance of 595 nm.

Absorbance of the ELISA signals from the standards indicated that the absorbance signal was directly proportional to the amounts of PAT present in each well. This data is represented in FIG. 5. The samples of the SUPERFECT® and *Agrobacterium*-mediated transformed plants show strong signals from the ELISA. These amounts are three times as high as the 10 ng/ml standard, the highest standard tested in the assay. These results indicate that PAT is expressed in the *Arabidopsis* transgenic plants that were transformed via SUPERFECT®-mediated plant transformation.

While this invention has been described in certain embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims and their equivalents.

What may be claimed is:

1. A method of introducing a nucleic acid of interest into a plant cell having a cell wall to effect stable transformation, the method comprising:
   providing the plant cell having a cell wall;
   interacting a polyamidoamine dendrimer and one or more cell penetrating peptides (CPPs), with a nucleic acid of interest to form an activated dendrimer structure;
   placing the plant cell having a cell wall and the activated dendrimer structure in contact with each other;
   allowing uptake of the activated dendrimer structure into the plant cell having a cell wall so as to introduce the nucleic acid of interest into the plant cell having a cell wall; and
   integrating the nucleic acid of interest into the genome of the plant cell having a cell wall so as to create a stable transformant.

2. The method according to claim 1, wherein interacting a polyamidoamine dendrimer with a nucleic acid of interest comprises assembly of the nucleic acid of interest onto a surface of the polyamidoamine dendrimer.

3. The method according to claim 1, wherein interacting a polyamidoamine dendrimer with a nucleic acid of interest comprises interacting negatively charged groups of the nucleic acid of interest with charged amino groups at a terminal end of the polyamidoamine dendrimer.

4. The method according to claim 1, further comprising allowing uptake of the activated dendrimer structure into a compartment of the plant cell having a cell wall.

5. The method according to claim 4, wherein the compartment is selected from the group consisting of cytosol, nucleus, tonoplasts, plastid, etioplast, chromoplast, leucoplast, elaioplast, proteinoplast, amyloplast, chloroplast, and a lumen of a double membrane.

6. The method according to claim 1, wherein the plant cell having a cell wall is selected from the group consisting of tobacco, carrot, maize, canola, rapeseed, cotton, palm, peanut, soybean, Oryza sp., Arabidopsis sp., Ricinus sp., and sugarcane cells.

7. The method according to claim 1, wherein the plant cell is from a tissue selected from the group consisting of embryos, meristematic cells, calli, pollen, leaves, anthers, roots, root tips, flowers, seeds, pods, and stems.

8. The method according to claim 1, further comprising derivatizing a surface of the polyamidoamine dendrimer.

9. The method according to claim 1, wherein the nucleic acid of interest comprises a component selected from the group consisting of nucleic acids, DNA, RNA, RNAi molecules, genes, plasmids, cosmids, YACs, BACs, and combinations thereof.

10. The method according to claim 8, wherein the nucleic acid of interest comprises a gene.

11. The method according to claim 9, wherein the gene is a foreign protein gene, an agronomic gene, or a marker gene.

12. The method according to claim 9, further comprising selecting cells that have stably integrated the nucleic acid of interest.

13. The method according to claim 12, wherein the selected cells are regenerable cells.

14. The method according to claim 13, further comprising regenerating a plant from the regenerable cells, wherein the regenerated plant or seeds therefrom comprise the nucleic acid of interest.

15. The method according to claim 1, wherein the polyamidoamine dendrimer comprises a dendrimer reagent.

16. A method of stably expressing a gene, the method comprising:
   providing a plant cell having a cell wall;
   interacting a polyamidoamine dendrimer and one or more CPPs, with a gene to form an activated dendrimer structure;
   placing the plant cell having a cell wall and the activated dendrimer structure in contact with each other;
   allowing uptake of the activated dendrimer structure into the plant cell having a cell wall, to obtain a stably transformed plant cell comprising the gene; and
   expressing the gene in progeny of a plant having the plant cell.

17. The method according to claim 16, wherein the gene is expressed in a chloroplast.

18. The method according to claim 16, further comprising selecting for cells stably expressing the gene prior to regenerating a plant from the stably transformed plant cell.

19. A method for transferring a plasmid DNA into a plant cell, comprising:
   interacting a polyamidoamine dendrimer and one or more CPPs, with a plasmid DNA to form an activated dendrimer structure; and contacting the activated dendrimer structure with an intact wall-bearing plant cell under conditions permitting uptake of the activated dendrimer structure into the plant cell.

20. The method of claim 19, further comprising stably expressing the gene in progeny of a plant having the plant cell.

* * * * *